United States Patent
Krishnan et al.

(10) Patent No.: US 12,383,586 B2
(45) Date of Patent: Aug. 12, 2025

(54) SPORE-BASED PROBIOTIC SUPPLEMENTATION IN DOGS AND CONTROL OF ENDOTOXEMIA

(71) Applicant: Novozymes A/S, Bagsvaerd (DK)

(72) Inventors: Kiran Krishnan, Saint Augustine, FL (US); Dale M. Kriz, Saint Augustine, FL (US); Thomas F. Bayne, Saint Augustine, FL (US)

(73) Assignee: Novozymes A/S, Bagsvaerd (DE)

( * ) Notice: Subject to any disclaimer, the term of this patent is extended or adjusted under 35 U.S.C. 154(b) by 0 days.

(21) Appl. No.: 18/627,241

(22) Filed: Apr. 4, 2024

(65) Prior Publication Data

US 2024/0307464 A1  Sep. 19, 2024

Related U.S. Application Data

(63) Continuation of application No. 17/023,097, filed on Sep. 16, 2020, now abandoned.

(60) Provisional application No. 62/900,901, filed on Sep. 16, 2019.

(51) Int. Cl.
| | |
|---|---|
| *A61K 35/744* | (2015.01) |
| *A61K 9/00* | (2006.01) |
| *A61K 35/742* | (2015.01) |
| *A61P 1/14* | (2006.01) |
| *A61P 31/04* | (2006.01) |

(52) U.S. Cl.
CPC .......... *A61K 35/744* (2013.01); *A61K 9/0053* (2013.01); *A61K 35/742* (2013.01); *A61P 1/14* (2018.01); *A61P 31/04* (2018.01)

(58) Field of Classification Search
None
See application file for complete search history.

(56) References Cited

U.S. PATENT DOCUMENTS

| | | |
|---|---|---|
| 2006/0008511 A1 | 1/2006 | Lin et al. |
| 2012/0052152 A1 | 3/2012 | Armentrout |
| 2012/0315249 A1 | 12/2012 | Olmstead |
| 2014/0023693 A1 | 1/2014 | Guenzburg et al. |
| 2015/0157670 A1 | 6/2015 | Kriz et al. |
| 2018/0289752 A1 | 10/2018 | Krishnan et al. |

FOREIGN PATENT DOCUMENTS

| | | |
|---|---|---|
| CN | 102651973 A | 8/2012 |
| CN | 103068254 A | 4/2013 |
| CN | 103764154 A | 4/2014 |
| CN | 104684408 A | 6/2015 |
| CN | 108371247 A | 8/2018 |
| WO | 2004080200 A1 | 9/2004 |
| WO | 2011069860 A1 | 6/2011 |
| WO | 2011075138 A1 | 6/2011 |
| WO | 2012170915 A1 | 12/2012 |
| WO | 2014020138 A2 | 2/2014 |

OTHER PUBLICATIONS

Anonymous, 2019, fidospore, 1-18—Tr.
Barko_2018_Journal_of_Veterinary_Internal_Medicine_32_9-25.
Bartko_2017_Pharmacological_research_125_215-223.
Biourge 1998 J. Nutrition 128(12 suppl) 2730S-2732S, 128(12 suppl).
CEAPA_2013_Best_Practice_&_Research_Clinical_Gastroenterology_27_139-155.
De Vries et al, 2013, International journal of Immunopathology and Pharmacology 26(4), 861-869.
Gallo_2016_World_journal_of_Gastroenterology_22_7186-7202.
Herstad_2010_Journal_of_small_animal_practice_51_34-38.
Jackson_1991_Lebensmittel-wissenschaft_technologie_24_289-297.
Kerns_2005_The_Canine_Digestion_Process_Whole_Dog_Journal.
Krishnan, 2017, AAPLI's nutrition guide to optimal health using principles of functional medicine and nutritional genomics, part 3, 269-286.
McFarlin et al., The American Journal of Gastroenteroloty, S657-S658, 2017.
McFarlin et al., World journal of Gastrointestinal Pathophysiology, 8(3), 117-126, 2017.
Schmitz_2016_Veterinary_medicine_and_science_2_71-94.
Van Deventer 1990 Blood 76(12) 2520-2526.
Vasanth 2015 Frontiers in immunology 6(article 409) 1-11, 409.
Wang, Journal of Hainan Medical University, 19(12)—Translation, 1781-1784, 2013.
Wang, Journal of Hainan Medical University, 19(12), 1781-1784, 2013.

*Primary Examiner* — Michelle F. Paguio Frising
*Assistant Examiner* — Grant C Currens
(74) *Attorney, Agent, or Firm* — Adam Rucker

(57) ABSTRACT

The present invention is directed to methods of administering a probiotic composition including *Bacillus subtilis*, *Bacillus licheniformis*, and *Pediococcus acidilactici* to dogs to decrease endotoxemia and improve the digestive process, and related methods.

14 Claims, 19 Drawing Sheets

CONSORT DIAGRAM REGARDING DOGS IN STUDY

PRE- AND POST-ADMINISTRATION DYNAMICS OF HEMATOLOGICAL PARAMETERS

IN HEALTHY DOGS AND DOGS WITH DYSBIOSIS

PRE- AND POST-ADMINISTRATION DYNAMICS OF HEMATOLOGICAL PARAMETERS IN HEALTHY DOGS AND DOGS WITH DYSBIOSIS

PRE- AND POST-ADMINISTRATION DYNAMICS OF HEMATOLOGICAL PARAMETERS
IN HEALTHY DOGS AND DOGS WITH DYSBIOSIS

PRE- AND POST-ADMINISTRATION DYNAMICS OF HEMATOLOGICAL PARAMETERS
IN HEALTHY DOGS AND DOGS WITH DYSBIOSIS

PRE- AND POST-ADMINISTRATION DYNAMICS OF BIOCHEMICAL PARAMETERS
IN HEALTHY DOGS AND DOGS WITH DYSBIOSIS

PRE- AND POST-ADMINISTRATION DYNAMICS OF BIOCHEMICAL PARAMETERS
IN HEALTHY DOGS AND DOGS WITH DYSBIOSIS

PRE- AND POST-ADMINISTRATION DYNAMICS OF BIOCHEMICAL PARAMETERS
IN HEALTHY DOGS AND DOGS WITH DYSBIOSIS

PRE- AND POST-ADMINISTRATION DYNAMICS OF BIOCHEMICAL PARAMETERS
IN HEALTHY DOGS AND DOGS WITH DYSBIOSIS

PRE- AND POST-ADMINISTRATION DYNAMICS OF BIOCHEMICAL PARAMETERS
IN HEALTHY DOGS AND DOGS WITH DYSBIOSIS

SPORE-BASED PROBIOTIC SUPPLEMENTATION IN DOGS AND CONTROL OF ENDOTOXEMIA

CROSS-REFERENCE TO RELATED APPLICATIONS

This application is a continuation of U.S. patent application Ser. No. 17/023,097 which claims priority or the benefit from U.S. Provisional Application Ser. No. 62/900,901, filed Sep. 16, 2019. The contents of these applications are fully incorporated herein by reference.

TECHNICAL FIELD

The present invention relates to methods of administering a probiotic composition including *Bacillus subtilis, Bacillus licheniformis*, and *Pediococcus acidilactici* to dogs to decrease endotoxemia and improve the digestive process, and related methods.

BACKGROUND

Interactions between the gut microbiota and host play an important role in the regulation of a multitude of physiological processes in many species, including domestic mammals, companion animals, and pets.

Probiotic compositions contain live microorganisms that are able to provide a beneficial effect on the host when administered in adequate amounts. The mechanisms by which these beneficial effects are achieved include reduced intestinal permeability, increased mucin secretion by goblet cells, increased production of defensins that prevent the colonization of pathogens, increased short-chain fatty acid production, stimulation of IgA secretion, decreased luminal pH and increased tolerance of immune cells for commensal microorganisms, while maintaining the ability to respond to pathogens (Gallo et al. "Modulation of microbiota as treatment for intestinal inflammatory disorders: An uptodate" *World J. Gastroenterol.* 22:7186-7202 (2016): Barko et al., "The gastrointestinal microbiome: a review" *J. Vet. Internal Med.* 32:9-25 (2018)). Non-viable microorganisms are also considered capable of conferring beneficial effects by adhering to the mucus layer of the gastrointestinal (GI) tract and stimulating immune functions (Barko et al., 2018).

Probiotic compositions benefit their host by supporting the proliferation of beneficial gut microflora. Probiotics are able to produce beneficial effects on their hosts without permanently modifying the microbiome, likely because of transient colonization in the intestine (Ceapa et al., "Influence of fermented mild products, prebiotics and probiotics on microbiota composition and health" *Best Pract. Res. Clin. Gastroenterol.* 27:139-155 (2013); Barko et al., 2018). Furthermore, probiotics may modulate the frequency of the tight junction proteins that act as a barrier in the intestinal paracellular pathway. By enhancing intestinal barrier function, probiotics serve as preventative agents to defend against adverse effects of pathogens, promoting positive effects on digestion and immune health. Additionally, it appears that the beneficial effects of probiotics may be strain-specific, with a majority of probiotic studies investigating *Bifidobacterium* and *Lactobacillus* strains in various special groups (i.e. diabetic, obese) of the general human population.

Members of the genus *Bacillus* are considered by some to have a higher probiotic potential compared to lactic acid-producing bacteria, because they have a high level of viability and are able to reproduce and increase in number in the GI tract, even in unfavorable environmental conditions of low pH. However, other researchers argue that a bacterium does not have to be viable to exert probiotic effects (Biourge et al., "The use of probiotics in the diet of dogs" J. Nutrition 128(12 Suppl): 2730S-2732S (1998); Schmitz and Suchodolski, "Understanding the canine intestinal microbiota and its modification by pro-, pre-, and synbiotics—what is the evidence?" *Vet. Med. Sci.* 2:71-94 (2016)).

Currently, probiotics are considered a potential alternative treatment for dogs with gut disorders such as leaky gut. Endotoxemia is a condition that is present in all mammals. It is characterized by an increase in serum endotoxin levels. It can affect either GI permeability, the GI microbiota, or both (McFarlin et al., 2015). In human medicine, it is known that this increase occurs about 5 hours after ingestion of a meal, and that it affects approximately 33% of the human population (Kirshnan, "Metabolic endotoxemia, A driving force behind chronic illness" *Aapi's nutrition guide to optimal health using principles of functional medicine & nutritional genomics, Part III:* 269-286 (2017)). In the case of dogs, mild endotoxemia levels were reported after intravenous infusion of low dose endotoxin (Bartko et al., "Selective glucocorticoid receptor modulation inhibits cytokine responses in a canine model of mild endotoxemia, *Pharmacolog. Res.* 125:215-223 (2017); De Vries et al., "Establishment of a Low Dose Canine Endotoxemia Model to Test Anti-Inflammatory Drugs: Effects of Prednisolone" *Intl. J. Immunopathol. and Pharmacol.* 26(4):861-869 (2013)), but naturally occurring endotoxemia has not been characterized. Experimentally induced endotoxemia has been studied in humans, using either a bolus injection of *Escherichia coli* endotoxin (Deventer et al., "Experimental endotoxemia in humans: analysis of cytokine release and coagulation, fibrinolytic, and complement pathways" *Blood* 76(12):2520-2526 (1990)) or by consuming a high-fat meal (McFarlin et al., "Oral spore-based probiotic supplementation was associated with reduced incidence of post-prandial dietary endotoxin, triglycerides, and disease risk biomarkers" World J. Gastrointest. Pathophysiol. 8:117-126 (2017)).

SUMMARY OF THE INVENTION

In an embodiment, the present invention is directed to a method of decreasing endotoxemia in a dog comprising the steps of: providing a probiotic composition comprising *Bacillus subtilis, Bacillus licheniformis*, and *Pediococcus acidilactici*, and administering the probiotic composition to the dog in an amount effective to decrease endotoxemia in the dog. In an embodiment, the present invention is also directed to improving digestion and the digestive process of dogs, and/or treating a digestive disorder in a dog.

In an embodiment, the present invention includes *Bacillus subtilis* HU58 and/or *Bacillus licheniformis* SL-307. In an embodiment, the total CFU of a discrete dose unit of the probiotic composition may be about 1 billion to about 10 billion CFU, including for instance about 2.5 to about 4 billion CFU. In an embodiment, a method of this invention may be used on a healthy dog, or on a dog with a gastrointestinal disorder, whether permanent or temporary.

DETAILED DESCRIPTION

Figure 1:
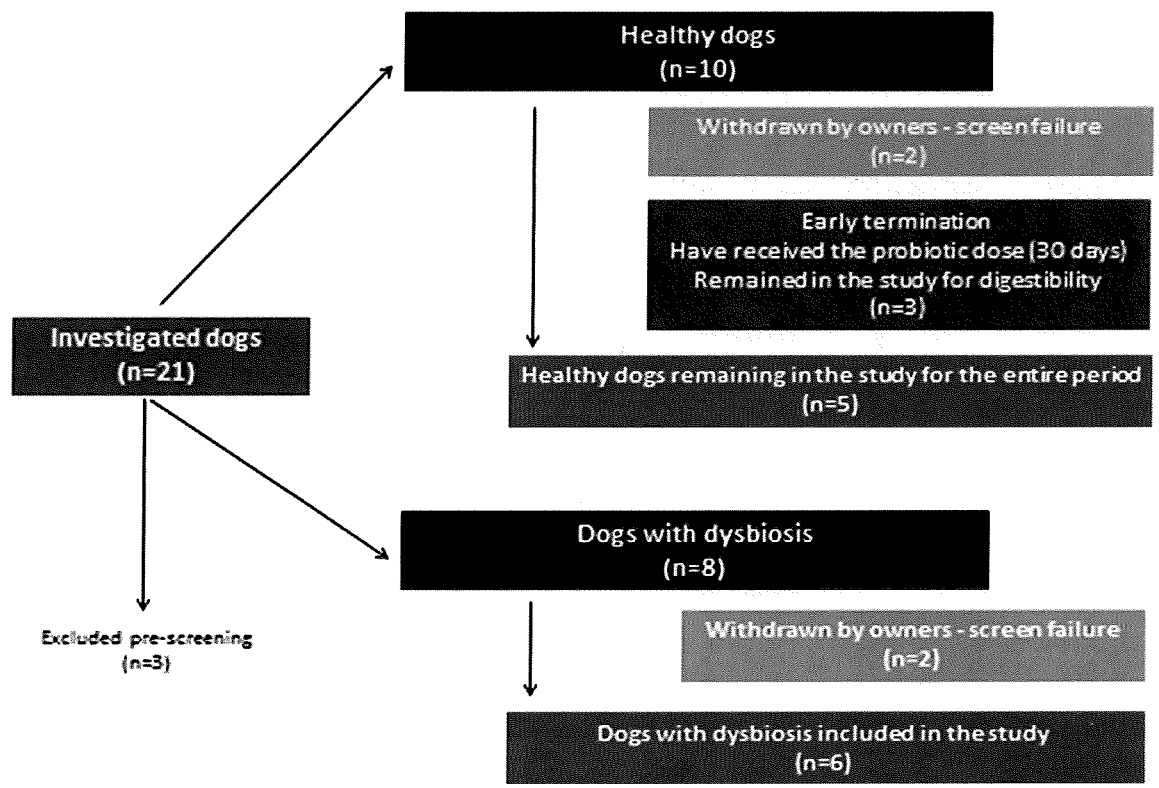
FIG. 1 is a consort diagram showing the enrollment and disposition of subjects according to this invention.

The present invention is directed to methods of administering a probiotic composition including *Bacillus subtilis*, *Bacillus licheniformis*, and *Pediococcus acidilactici* to dogs.

The below definitions and discussion are intended to guide understanding but are not intended to be limiting with regard to other disclosures in this application. References to percentage (%) in compositions of the present invention are to the % by weight of a given component to the total weight of the composition being discussed, also signified by "w/w", unless stated otherwise.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, an "effective amount" or an "amount effective for" is defined as an amount effective, at dosages and for periods of time necessary, to achieve a desired biological result, such as reducing, preventing, or treating a disease or condition and/or inducing a particular beneficial effect. The effective amount of compositions of the disclosure may vary according to factors such as age, sex, and weight of the individual. Dosage regime may be adjusted to provide the optimum response. Several divided doses may be administered daily, or the dose may be proportionally reduced as indicated by the exigencies of an individual's situation. A single daily dose may be administered in an effective amount of *Bacillus subtilis, Bacillus licheniformis,* and *Pediococcus acidilactici* according to this invention. As will be readily appreciated, a composition in accordance with the present disclosure may be administered in a single serving or in multiple servings spaced throughout the day. As will be understood by those skilled in the art, servings need not be limited to daily administration, and may be on every second or third day or other convenient effective basis. The administration on a given day may be in a single serving or in multiple servings spaced throughout the day depending on the exigencies of the situation.

According to the present invention, a "subject", "patient" or other individual according to this invention is a dog.

A "probiotic composition" of this invention includes *Bacillus subtilis, Bacillus licheniformis,* and *Pediococcus acidilactici*. A probiotic composition of this invention may comprise, consist essentially of, or consist of *Bacillus subtilis, Bacillus licheniformis,* and *Pediococcus acidilactici*. In an embodiment, a probiotic composition of this invention is Fidospore®, an encapsulated dietary supplement including 4 billion CFU total of Bacillus subtilis HU58, *Bacillus licheniformis* SL-307, and *Pediococcus acidilactici*, along with 180 mg defatted grass-fed beef liver extract per capsule. HU58 ("ProBiotene™") is a strain of *Bacillus subtilis*, a preparation of which is manufactured by Viridis BioPharma Pvt. Ltd., Mumbai, India. *Bacillus subtilis* HU58 has been deposited with the National Center for Biotechnology Research under the accession number EF101709. The *Bacillus* Genetic Stock Center ("BGSC") assigned number for *Bacillus* HU58 is 3A34, and the NCIMB Ltd. Assigned strain number is 30283. A strain of *Bacillus licheniformis* is also used in the probiotic composition of this invention. A strain of *Pediococcus acidilactici* is also used in the probiotic composition of this invention. In an embodiment, a probiotic composition of this invention includes about 2 billion CFUs HU58, about 500 million to 1 billion CFUs *Pediococcus acidilactici,* and 100 million CFUs of *Bacillus licheniformis*, administered in a capsule once per day, orally; in an embodiment, such composition is Fidospore®. In an embodiment, a capsule of this invention is made of cellulose. In various embodiments, the present disclosure discloses probiotic compositions and methods of producing and using these probiotic compositions. In other embodiments, a probiotic composition of this invention supports digestive health, reduces endotoxemia, and/or treats digestive disorders in dogs.

These effects have been experimentally verified based on supplementation of study participants with a composition comprising one or more colonizing probiotic material strains that may be spore-based probiotic bacterial strains.

Probiotic compositions of this invention may be measured by colony forming units ("CFUs"). Effective dosages are usually in the hundreds of millions of CFUs or higher. If probiotics are being used to help with digestion, probiotics should be taken with meals, but otherwise the probiotics may survive if taken between meals, particularly if taken with liquids that help to dilute stomach acid and move the probiotics more quickly into the digestive tract. Probiotics may be given short-term or long-term.

In some embodiments, the concentration of probiotic microorganisms in the composition may be at least about $1 \cdot 10^9$ CFU/g, at least about $2 \cdot 10^9$ CFU/g, at least about $3 \cdot 10^9$ CFU/g, at least about $4 \cdot 10^9$ CFU/g, at least about $5 \cdot 10^9$ CFU/g, at least about $6 \cdot 10^9$ CFU/g, at least about $7 \cdot 10^9$ CFU/g, at least about $8 \cdot 10^9$ CFU/g, at least about $9 \cdot 10^9$ CFU/g, at least about $1 \cdot 10^{10}$ CFU/g, at least about $2 \cdot 10^{10}$ CFU/g, at least about $3 \cdot 10^{10}$ CFU/g, at least about $4 \cdot 10^{10}$ CFU/g, at least about $5 \cdot 10^{10}$ CFU/g, at least about $6 \cdot 10^{10}$ CFU/g, at least about $7 \cdot 10^{10}$ CFU/g, at least about $8 \cdot 10^{10}$ CFU/g, at least about $9 \cdot 10^{10}$ CFU/g, or at least about $1 \cdot 10^{11}$ CFU/g, and any range therein.

In an embodiment, the spore-based probiotic composition may comprise spores having a survival rate within any of the following ranges after exposure to gastric acid in situ: about 75% to about 99%, about 80% to about 95%, about 85% to about 90%, and greater than about 90%. The spore-based probiotic composition may comprise a number of spores within any of the following ranges: about 1 billion to about 10 billion spores, about 1.5 billion spores to about 9.5 billion spores, about 2.5 billion spores to about 8 billion spores, about 3 billion spores to about 7 billion spores, about 3.5 billion spores to about 6 billion spores, about 4 billion spores to about 5 billion spores, and about 4 billion spores.

In an embodiment, the spore-based probiotic composition may comprise a liquid, confectionary item, powder or pill form or may be added to a food product or formulated as a dietary supplement. For instance, in an embodiment, the probiotic composition may be in powder form and added to dog food. In one implementation, about $1 \cdot 10^{10}$ CFU of microorganism is present in each gram of bulk, dried raw powder where each gram contains about 60% or less of bacterial mass and about 40% carrier system. In other implementations, each gram contains about 70% or less of bacterial mass and about 30% carrier system, about 80% or less of bacterial mass and about 20% carrier system, about 90% or less of bacterial mass and about 10% carrier system, about 50% or less of bacterial mass and about 50% carrier system, about 40% or less of bacterial mass and about 60% carrier system, about 30% or less of bacterial mass and about 70% carrier system, about 20% or less of bacterial mass and about 80% carrier system, or about 10% or less of bacterial mass and about 90% carrier system.

Implementations of the methods and compositions disclosed herein may comprise a sporebased probiotic. A spore-based probiotic is comprised of endosomes which are highly resistant to acidic pH, are stable at room temperature, and deliver a much greater quantity of high viability bacteria to the small intestine than traditional probiotic supplements. Traditional microencapsulation uses live microorganisms which are then micro-encapsulated in an effort to protect the microorganisms; however, this is a process that inherently leads to the eventual death of the microorganisms thereby reducing the efficacy of the microorganisms. Using spore-based microorganisms that have been naturally microencapsulated to form endosomes may be preferable as these microorganisms are dormant and do not experience a degradation in efficacy over time.

These spore-based microorganisms are also particularly thermally stable and can survive UV pasteurization, so they are also able to be added to food products or beverages prior to thermal exposure or UV pasteurization without experiencing a degradation in efficacy over time.

Micro-Encapsulation

In certain implementations, the probiotic microorganisms are microencapsulated prior to addition to the probiotic compositions. Micro-encapsulation is a process in which tiny particles or droplets are surrounded by a coating to give small capsules of many useful properties. In a relatively simple form, a microcapsule is a small sphere with a uniform wall around it. The material inside the microcapsule is referred to as the core, internal phase, or fill, whereas the wall is sometimes called a shell, coating, or membrane. Most microcapsules have diameters between a few micrometers and a few millimeters.

The definition of "microencapsulation" has been expanded, and includes most foods. Every class of food ingredient has been encapsulated; flavors are the most common. The technique of microencapsulation depends on the physical and chemical properties of the material to be encapsulated. See, e.g., L.S. Jackson & K. Lee, *Microencapsulation and the food industry*, LEBENSMITTEL-WISSENSCHAFT TECHNOLOGIE (Jan. 1, 1991), incorporated by reference herein for the purposes of describing microencapulation.

Many microcapsules, however, bear little resemblance to these simple spheres. The core may be a crystal, a jagged absorbent particle, an emulsion, a Pickering emulsion, a suspension of solids, or a suspension of smaller microcapsules. The microcapsule even may have multiple walls. Various techniques may be used to produce microcapsules, and each of such various techniques will be understood by a person of ordinary skill in the art. These techniques that may be used to produce microcapsules include, but are not limited to, pan coating, air-suspension coating, centrifugal extrusion, vibrational nozzle, spray-drying, ionotropic gelation, interfacial polycondensation, interfacial cross-linking, in situ polymerization, and matrix polymerization, as described below.

Pan Coating

The pan coating process, widely used in the pharmaceutical industry, is among the oldest industrial procedures for forming small, coated particles or tablets. The particles are tumbled in a pan or other device while the coating material is applied slowly.

Air-Suspension Coating

Air-suspension coating, first described by Professor Dale Eavin Wurster at the University of Wisconsin in 1959, gives improved control and flexibility compared to pan coating. In this process, the particulate core material, which is solid, is dispersed into the supporting air stream and these suspended particles are coated with polymers in a volatile solvent leaving a very thin layer of polymer on them. This process is repeated several hundred times until the required parameters such as coating thickness, etc., are achieved. The air stream which supports the particles also helps to dry them, and the rate of drying is directly proportional to the temperature of the air stream which can be modified to further affect the properties of the coating.

The re-circulation of the particles in the coating zone portion is effected by the design of the chamber and its operating parameters. The coating chamber is arranged such that the particles pass upwards through the coating zone, then disperse into slower moving air and sink back to the base of the coating chamber, making repeated passes through the coating zone until the desired thickness of coating is achieved.

Centrifugal Extrusion

Liquids are encapsulated using a rotating extrusion head containing concentric nozzles. In this process, a jet of core liquid is surrounded by a sheath of wall solution or melt. As the jet moves through the air it breaks, owing to Rayleigh instability, into droplets of core, each coated with the wall solution. While the droplets are in flight, a molten wall may be hardened or a solvent may be evaporated from the wall solution. Because most of the droplets are within +10% of the mean diameter, they land in a narrow ring around the spray nozzle. Hence, if needed, the capsules can be hardened after formation by catching them in a ring-shaped hardening bath. This process is excellent for forming particles 400-2,000 μm in diameter. Because the drops are formed by the breakup of a liquid jet, the process is only suitable for liquid or slurry. A high production rate can be achieved, i.e., up to 22.5 kg (50 lb) of microcapsules can be produced per nozzle per hour per head. Heads containing 16 nozzles are available.

Vibrational Nozzle

Core-Shell encapsulation or Microgranulation (matrix-encapsulation) can be done using a laminar flow through a nozzle and an additional vibration of the nozzle or the liquid. The vibration has to be done in resonance of the Rayleigh instability and leads to very uniform droplets. The liquid can consist of any liquids with limited viscosities (0-10,000 mPa·s have been shown to work), e.g., solutions, emulsions, suspensions, melts, etc. The solidification can be done according to the used gelation system with an internal gelation (e.g., sol-gel processing, melt) or an external (additional binder system, e.g., in a slurry). The process works very well for generating droplets between 20-10,000 μm, applications for smaller and larger droplets are known. The units are deployed in industries and research mostly with capacities of 1-20,000 kg per hour (2-44,000 lb/h) at working temperatures of 20-1500° C. (68-2732° F.) (room temperature up to molten silicon). Nozzle heads with from one up to several hundred thousand nozzles are available.

Spray-Drying

Spray drying serves as a microencapsulation technique when an active material is dissolved or suspended in a melt or polymer solution and becomes trapped in the dried particle. The main advantages are the abilities to handle labile materials because of the short contact time in the dryer; in addition, the operation is economical. In modern spray dryers the viscosity of the solutions to be sprayed can be as high as 300 mPa·s. By combining this technique with the use of supercritical Carbon Dioxide, sensitive materials like proteins can be encapsulated.

Ionotropic Gelation

The coacervation-phase separation process consists of three steps carried out under continuous agitation:
(1) Formation of 3 immiscible chemical phases: liquid manufacturing vehicle phase, core material phase, and coating material phase.
(2) Deposition of coating: core material is dispersed in the coating polymer solution. Coating polymer material coated around core. Deposition of liquid polymer coating around core by polymer adsorbed at the interface formed between core material and vehicle phase.
(3) Rigidization of coating: coating material is immiscible in vehicle phase and it gets rigid in form. Techniques for rigidization include thermal, cross-linking, or dissolvation.

Interfacial Polycondensation

In interfacial polycondensation, the two reactants in a polycondensation meet at an interface and react rapidly. The basis of this method is the classical Schotten-Baumann reaction between an acid chloride and a compound containing an active hydrogen atom, such as an amine or alcohol, a polyester, a polyuria, or a polyurethane. Under the right conditions, thin flexible walls form rapidly at the interface. A solution of the pesticide and a diacid chloride are emulsified in water and an aqueous solution containing an amine and a polyfunctional isocyanate is added. Base is present to neutralize the acid formed during the reaction. Condensed polymer walls form instantaneously at the interface of the emulsion droplets.

Interfacial Cross-Linking

Interfacial cross-linking is derived from interfacial polycondensation, and was developed to avoid the use of toxic diamines, for pharmaceutical or cosmetic applications. In this method, the small bifunctional monomer containing active hydrogen atoms is replaced by a biosourced polymer, like a protein. When the reaction is performed at the interface of an emulsion, the acid chloride reacts with the various functional groups of the protein, leading to the formation of a membrane. The method is very versatile, and the properties of the microcapsules (size, porosity, degradability, mechanical resistance) may be varied. Flow of artificial microcapsules in microfluoridic channels is contemplated.

In-Situ Polymerization

In a few microencapsulation processes, the direct polymerization of a single monomer is carried out on the particle surface. In one process, e.g., cellulose fibers are encapsulated in polyethylene while immersed in dry toluene. Usual deposition rates are about 0.5 μm/min. Coating thickness ranges 0.2-75 μm (0.0079-3.0 mils). The coating is uniform, even over sharp projections. Protein microcapsules are biocompatible and biodegradable, and the presence of the protein backbone renders the membrane more resistant and elastic than those obtained by interfacial polycondensation.

Matrix Polymerization

In a number of processes, a core material is imbedded in a polymeric matrix during formation of the particles. A simple method of this type is spray-drying, in which the particle is formed by evaporation of the solvent from the matrix material. However, the solidification of the matrix also can be caused by a chemical change.

In an embodiment, "administering", "administration", and the like, refers to providing a probiotic composition of this invention to a subject so that *Bacillus subtilis, Bacillus licheniformis*, and *Pediococcus acidilactici* may reach the subject's gastrointestinal tract and, directly and/or for instance through production and release of metabolites or other active chemicals, act on tissues and/or cells of the GI tract and/or in the GI tract (such as bacteria) to decrease endotoxemia, improve the digestive process, and/or treat gastrointestinal disorders. In an embodiment, the subject is a healthy dog or a dog with a GI tract disorder. Administration to a subject according to this invention may be oral, for instance in the form of a dietary supplement, in a solid dosage form such as a capsule or in a liquid dosage form and/or administered via other routes such as rectally as a suppository. In an embodiment, a probiotic composition of this invention, such as Fidospore®, is taken orally before, with, or after a meal. "Coadministration" refers to administering a probiotic of this invention at the same time including the same day, for instance with an antibiotic or other substance that may be detrimental to gut health, or for instance with another substance beneficial to gut health.

In an embodiment, a "dietary supplement" according to the present invention refers to a probiotic composition of this invention, which is administered orally as an addition to a subject's diet, which is not a natural or conventional food. In an embodiment, the dietary supplement includes an effective amount of *Bacillus subtilis, Bacillus licheniformis,* and *Pediococcus acidilactici*, such that these substances when administered to a dog enter the dog's digestive tract and act in the dog's digestive tract and elsewhere in the body as appropriate to decrease endotoxemia, improve the digestive process, and/or treat gastrointestinal disorders.

In an embodiment, a dietary supplement or other form of a probiotic composition of this invention is administered daily for 1 day, 1-7 days, 1-14 days, 1-30 days, 1-31 days, 1-32 days, 1-60 days, or for another period of time. In an embodiment, the probiotic composition may be taken chronically, for instance daily or weekly for several months or a year or years.

In an embodiment, a probiotic composition of this invention may be administered to treat intestinal dysbiosis, endotoxemia, or other disorders of the GI tract of a subject.

In an embodiment, a probiotic composition of this invention may be administered to prevent intestinal dysbiosis, endotoxemia, or other disorders of the GI tract of a subject.

In an embodiment, a probiotic composition of this invention may be administered to improve the health and digestion of the GI tract of a subject.

The present invention may be further understood in connection with the following Example and embodiments. The Example and embodiments described throughout this application are provided to illustrate the invention and are not intended as limiting.

EXAMPLE

In this Example, a spore-based probiotic composition according to this invention, containing *Bacillus subtilis, Bacillus licheniformis*, and *Pediococcus acidilactici*, reduced endotoxemia in dogs after 30 days of administration. Also, a pattern of natural post-meal endotoxemia levels in clinically healthy dogs and in those with apparent dysbiosis is identified.

Study Design

A total of 18 adult dogs aged between 4 months and 7 years of age were enrolled in the study. The dogs were administered a probiotic composition comprising *B. subtilis, B. licheniformis*, and *P. acidilactici* once daily with a meal for 30 days (See Table 1).

On day −5 to day 0, feces collection from healthy dogs began.

On day 0 of the study, the dogs were clinically examined and fecal and blood samples were collected. For the detection of endotoxemia, blood samples were collected pre-meal and post-meal (6 hours and 12 hours). Clinical examinations were conducted by a veterinarian with the aim of evaluating the general health of each dog. The examinations included collection of temperature, cardiac rate, and respiratory rate data.

Between day 1 and day 30, the probiotic composition was administered to the animals according to manufacturer recommendations. On day 31, all dogs were clinically examined as described above and biological samples (feces and blood) were collected for paraclinical exams. For the detection of endotoxemia, blood samples were collected pre-meal and post-meal (6 hours and 12 hours).

Between days 31 and 36, feces was collected from healthy dogs at least for digestibility studies.

TABLE 1

Study Schedule

| Day | Experimental Time | Activities |
|---|---|---|
| Day −5 to Day 0 | Fecal sample collection | Fecal testing, healthy dogs |
| Day 0 | Blood collection 1: pre-meal<br>Blood collection 2: 6 hours post-meal<br>Blood collection 3: 12 hours post-meal | Clinical examination, collection of biological samples (blood and fecal) |
| Day 1 to Day 30 | Probiotic composition administration<br>Determine fecal score (Days 1, 7, 15, 30) | |
| Day 31 | Blood collection 1: pre-meal<br>Blood collection 2: 6 hours post-meal<br>Blood collection 3: 12 hours post-meal | Clinical examination, collection of biological samples (blood and fecal) |
| Day 31 to 36 | Fecal sample collection | Fecal testing, healthy dogs |

Study Population

This study used real-world clinical cases, as shown in FIG. 1. FIG. 1 shows patient disposition. Patients were carefully screened using the study exclusion/inclusion criteria described below. Qualified dogs were enrolled in the study. Of the 18 dogs that were enrolled in the study, a total of 11 dogs completed the entire study period: 5 (five) healthy dogs (Table 2) and 6 (six) dogs with dysbiosis (Table 3). Throughout the course of the study, the dogs did not experience any lifestyle or nutritional changes.

Inclusion criteria for the healthy dogs included the absence of GI manifestations (diarrhea, vomiting), no history of antibiotic treatment in the last 6 months, clinically healthy, and normally consumed 1 meal per day. Dogs were excluded from the healthy dog group if they had acute liver or kidney disease, intestinal endoparasitism, or antibiotic treatment in the last 6 months.

For the dogs with intestinal dysbiosis, inclusion criteria were current antibiotic treatment (minimum duration of 2 weeks) or the presence of GI manifestations (diarrhea, vomiting), and normally consumed one meal per day. Dogs were excluded if they had acute liver or kidney disease or if they had intestinal endoparasitism.

TABLE 2

Healthy dogs

| Patient Code | Breed | Age | Sex | Observations |
|---|---|---|---|---|
| 01-K | Czechoslovakian wolfdog | 4 years | Castrated Male | Current on all vaccinations. No specific external or internal treatment was needed. |
| 02-H | Mixed breed dog | 1.8 years | Female | |
| 03-L* | Border collie | 3 years | Female | |
| 04-N* | Shetland shepherd | 1 year | Female | |
| 05-D* | Shetland shepherd | 7 years | Female | |
| 06-A | Akita Inu | 5 years | Female | |
| 07-I | Akita Inu | 2 years | Female | |
| 08-C | Akita Inu | 1.5 years | Female | |

*early termination; received the probiotic dose; remained in the study only for fecal score and digestibility study

TABLE 3

Dogs With Intestinal Dysbiosis

| Patient Code | Breed | Age | Sex | Observations/diagnosis |
|---|---|---|---|---|
| 09-B | Labrador | 7 months | Male | Recurrent diarrhea/vomiting |
| 10-Y | Akita Inu | 5.9 years | Female | Diarrhea/chronic pancreatitis |
| 11-L | Labrador | 4 months | Male | Dermatitis/antibiotic treatment (enrofloxacin, 14 days) |
| 12-D | Boxer | 2 years | Male | Recurrent diarrhea induced by stress |
| 13-U | Akita Inu | 4.5 years | Male | Recurrent diarrhea |
| 14-M | Swiss White Shepherd | 3 years | Castrated Male | Recurrent diarrhea |

Treatment

The probiotic product tested comprised two strains of bacteria: *B. subtilis* HU58 and *P. acidilactici* (FidoSpore™). The probiotic was given in capsules. One capsule was administered per day with the daily meal for 30 days. Liver powder was used to improve the taste of the probiotic product and to ensure it was ingested.

Clinical Investigations

To evaluate the health of the dogs entering the study and to obtain baseline clinical data, each dog was given a clinical evaluation. A general clinical examination, which included collection of data related to clinical parameters was performed on the dogs. The normal range values for dogs in the Merck Veterinary Manual (2016) were considered normal clinical values in this study.

Fecal Score

During probiotic treatment, dog owners were asked to complete the Optidigest clinical sheet made by Purina (www.purina.com; original sheet may be available at https://www.purina.ro/produse/proplan-optidigest). The clinical sheet was divided in three parts: stool consistency, stool volume and smell, and gut rambling and flatulence.

The stool consistency part assessed the stool of the dog during one full day using a fecal score scale. The scale is described as follows: 1—very hard and dry, 2—firm but not hard, 3—log-like, 4—very moist, 5—very moist but has distinct shape, 6—has texture but no defined shape, 7—watery no texture, flat.

The stool volume and smell part was also recorded during a full day. The volume is graded as 1—small, 2—normal, 3—large, 4—very large. Smell is recorded as 1—very little odor, 2—low odor, 3—moderately unpleasant smell, 4—unpleasant smell, 5—very unpleasant smell.

The gut rumbling and the flatulence part was evaluated during the day and their presence or absence were recorded.

All these data were filled day 1, day 7, day 15, and day 30 of the study.

Digestibility

The digestibility of fodders is measured using the digestibility coefficient (D.C.) which represents the portion of a feed or nutrient of feed which is not recovered in feces, i.e., the portion which has been absorbed by the animal. Equation I was used for determinations of Apparent Digestibility Coefficient (ADC %):

$$\text{Apparent} - ADC(\%) = \frac{\text{INTAKE} - \text{EXCRETION}}{\text{INTAKE}} \times 100\% \qquad \text{EQN. I}$$

Starting from this principle, levels for the following were determined: dry matter (DM), crude protein—Kjeldahl method (CP), crude fat—Soxhlet method (CF), crude cellulose—Weende method (CC), nitrogen free extract (NFE).

Digestibility was determined only in healthy dogs. Biological samples were feces and food samples. Feces were collected 5 days before the start of treatment and 5 days after the end of administration of the probiotic composition.

Paraclinical Investigations

Parasitology

A coprology examination was performed on the 11 dogs enrolled in this study before and after the administration of probiotics. The technique of flotation (Willis method) and sedimentation are used. The objective is to see if the probiotics effect is not misinterpreted with the presence of internal parasites.

Hematological Parameters

Blood was collected in hematologic tubes with an anticoagulant (EDTA). The hematologic samples were analyzed by the device ABACUS JUNIOR VET (Table 4). All data obtained were compared with references from the Merck Veterinary Manual (2016).

These evaluations were performed ante-(day 0) and post-administration (day 31) of the probiotic composition (Table 5).

TABLE 4

Hematologic parameters and their methods

| No. | Parameter | The method |
|---|---|---|
| 1 | Hematocrit (HCT) | Calculated from RBC and MCV, HCT = RBC × MCV × 100 |
| 2 | Hemoglobin (HGB) | Measured photometrically |
| 3 | Red blood cell count (RBC) | Number of erythrocytes |
| 4 | Mean corpuscular volume (MCV) | Average volume of individual erythrocytes derived from the RBC histogram |
| 5 | Mean corpuscular hemoglobin (MCH) | MCH = HGB/RBC |
| 6 | Mean corpuscular hemoglobin concentrations (MCHC) | MCHC = [HGB/HCT] × 100 |
| 7 | Total white blood cell count (WBC) | Number of leucocytes |
| 8 | Differential white cell count | Smear/Microscopy |

TABLE 5

BLOOD SAMPLE INVESTIGATION (HEALTHY DOGS AND DOGS WITH DYSBIOSIS)

| | Blood/serum investigations | Ante-probiotic administration (day 0) | | | Post-probiotic administration (day 31) | | |
|---|---|---|---|---|---|---|---|
| | | Ante-meal | Post meal 6 h | Post meal 12 h | Ante-meal | Post meal 6 h | Post meal 12 h |
| Healthy Dogs | Hematology | x | — | — | x | — | — |
| | Biochemistry | x | — | — | x | — | — |
| | Endotoxemia | x | x | x | x | x | x |
| | IL-1 β | x | — | — | x | x* | x* |
| | CD14 | x | — | — | x | x* | x* |
| Dogs with dysbiosis | Hematology | x | — | — | x | — | — |
| | Biochemistry | x | — | — | x | — | — |
| | Endotoxemia | x | x | x | x | x | x |
| | IL-1 β | x | x | x | x | x | x |
| | CD14 | x | x | x | x | x | x |

*only for 3 dogs

Biochemical Parameters

A Vet Scan Chemistry Analyzer was used with Comprehensive Tests which provided quantitative determinations of the following: alanine aminotransferase (ALT), albumin (ALB), alkaline phosphatase (ALP), amylase (AMY), total calcium ($CA^{++}$), creatinine (CRE), globulin (GLOB), glucose (GLU), phosphorus (PHOS), potassium (K+), sodium (NA+), total bilirubin (TBIL), total protein (TP), and urea nitrogen (BUN) in heparinized whole blood, heparinized plasma, or serum. All data obtained were compared with references from the Merck Veterinary Manual (2016).

These evaluations were performed ante-(day 0) and post-administration (day 31) of the probiotic composition (Table 5).

Determination of Endotoxemia

To assay for endotoxemia, we used the ToxinSensor™ Chromogenic LAL Endotoxin Assay Kit (GenScript, Piscataway NJ (USA)). This method utilizes a modified Limulus Amebocyte Lysate and a synthetic color producing substrate to detect endotoxin chromogenically. The end-product can be measured using a spectrophotometer (545 nm filter) and endotoxin levels can be determined by comparing to a standard curve. The kit has a minimum endotoxin detection limit of 0.01 EU/mL and a measurable concentration range of 0.01 to 1 EU/mL.

Endotoxemia evaluation was performed for all dogs (healthy and with dysbiosis). The study protocol included endotoxemia evaluation in pre-meal and post-meal (6 hours and 12 hours) serum daily probiotic administration. (Table 5). Endotoxemia was assessed using serum as follows: undiluted serum, serum diluted 1:1, serum diluted 1:2. These evaluations were performed ante-(day 0) and post-administration (day 31) of the probiotic composition. (Table 5). Results were calculated according to the standard curve ($R^2=0.9808$) for the 1:2 dilution of the serum.

Immune/Inflammatory Parameters

For investigation of immune/inflammatory parameters we used:

Canine IL-1 β (Interleukin 1 Beta) ELISA Kit-The results were calculated according to the standard curve ($R^2=0.9527$).

Nori Canine CD14 ELISA Kit-The results were calculated according to the standard curve ($R^2=0.991$).

Canine IL-6 (Interleukin 6) ELISA Kit-For this parameter, values of OD were not within the standard curve and the results could not be interpreted.

The evaluation of IL1B (Interleukin-1-beta, a pro-inflammatory cytokine important in host-defense responses to infection and injury) and CD14 (a key molecule in activating innate immune cells) was performed for all dogs (healthy and with dysbiosis). The protocol of investigations was the same as for endotoxemia. For the dogs with dysbiosis the investigation protocol included evaluation of this parameter, in dynamics, anteprandial and postprandial (6 and 12 hours). These evaluations were performed ante-(day 0) and post-administration (day 31) of the probiotic composition (Table 5).

For the healthy dog group, because of the hemolysis of some blood samples and modification of the protocol, we have the complete dynamic only for the results of ante-(day 0) and post-administration (day 31) of the probiotic composition, without the dates before and 6 or 12 hours after a meal (Table 5).

Statistical Analysis

Data were analyzed using a conditional analysis of variance (ANOVA) and the following conditions (EQN. II):

$$(\text{healthy dogs or dogs with dysbiosis}) \times (\text{experiment time (day 0 and day 31)}) \times (\text{meal time (pre-meal, 6 hours post-meal, 12 hours post-meal)}). \quad \text{EQN. II}$$

Significance was set at p<0.05, which was determined using the Student-Newman-Keuls Multiple Comparisons Test. Changes in study parameters were determined using linear regression by trend line and expression of $R^2$.

RESULTS

Clinical Examination

A general clinical examination was performed on all study dogs before starting the probiotic treatment (day 0) and at the end of the study (day 31).

All dogs presented with no significant treatment needs during the clinical examination. All study dogs had a normal temperature, ranging between 37.9° C. and 39.9° C. Cardiac rates did not indicate any issues of significant clinical importance. All of the study dogs presented with a higher than normal value for respiratory rate. The normal at rest value for respiratory rate for dogs is between 18 and 34 breaths per minute. The increased respiratory rate was not alarming and may be explained by excitement, stress, and/or a high temperature in the examination room.

The clinical appearance of the healthy dogs was not altered by treatment with the probiotic composition of the present invention. No symptoms such as diarrhea or vomiting were observed in the healthy dogs. Probiotic treatment improved the appearance of the dog's fur and induced improvement of skin lesions.

For the dogs with dysbiosis, initial clinical examinations revealed diarrhea, vomiting, and/or skin lesions; clinical symptoms varied depending on the symptoms that qualified each dog for inclusion in the study. After completion of 30 days of treatment with a probiotic composition of this invention, we observed a decrease in digestive symptoms and in some cases the disappearance of digestive problems. Improvements were observed in the general condition of these dogs, with details of the improvements depending on the original diagnosis for each dog. In dog 10-Y (See Table 3), improvement in health status was observed at the completion of 30 days of treatment with a probiotic composition of this invention and the owner requested continued treatment for an additional 30 days.

Fecal Score

During treatment with the probiotic composition of this invention, the dog's owners were asked to fulfill the Optidigest clinical sheet made by Purina. As discussed above, this clinical sheet is divided in three parts: stool consistency, stool volume and smell, and gut rambling and flatulence.

In most dogs, stool consistency and stool volume slightly improved with treatment of a probiotic composition of this invention. According to the Optidigest sheet results the stool's smell didn't improve with treatment from the probiotic composition of this invention. Gut rumbling wasn't present in any of the dogs before, during, or after treatment with the probiotic composition of this invention. However, flatulence seemed to improve in the only dog that presented flatulence before the treatment (See Table 6, Table 7).

TABLE 6

Fecal score for healthy dogs

| | Day 1 | Day 7 | Day 15 | Day 30 |
|---|---|---|---|---|
| 01-K | | | | |
| Stool Consistency | 4 | 3 | 2 | 2 |
| Stool Volume | 2 | 2 | 2 | 1 |
| Stool Smell | 2 | 2 | 2 | 1 |
| Gut rumbling | − | − | − | − |
| Flatulence | − | − | − | − |
| 02-H | | | | |
| Stool Consistency | 4 | 3 | 3 | 3 |
| Stool Volume | 3 | 2 | 2 | 2 |
| Stool Smell | 3 | 3 | 3 | 3 |
| Gut rumbling | − | − | − | − |
| Flatulence | − | − | − | − |
| 03-L | | | | |
| Stool Consistency | 6 | 5 | 5 | 5 |
| Stool Volume | 2 | 2 | 2 | 2 |
| Stool Smell | 3 | 3 | 3 | 3 |
| Gut rumbling | − | − | − | − |
| Flatulence | + | + | − | − |
| 04-N | | | | |
| Stool Consistency | 5 | 5 | 5 | 5 |
| Stool Volume | 2 | 2 | 2 | 2 |
| Stool Smell | 3 | 3 | 3 | 3 |
| Gut rumbling | − | − | − | − |
| Flatulence | − | − | − | − |
| 05-H | | | | |
| Stool Consistency | 5 | 5 | 4 | 4 |
| Stool Volume | 2 | 2 | 2 | 2 |
| Stool Smell | 2 | 2 | 3 | 3 |
| Gut rumbling | − | − | − | − |
| Flatulence | − | − | − | − |
| 06-A | | | | |
| Stool Consistency | 4 | 3 | 3 | 3 |
| Stool Volume | 3 | 2 | 2 | 2 |
| Stool Smell | 3 | 3 | 3 | 3 |
| Gut rumbling | − | − | − | − |
| Flatulence | − | − | − | − |
| 07-I | | | | |
| Stool Consistency | 4 | 3 | 3 | 3 |
| Stool Volume | 3 | 2 | 2 | 2 |
| Stool Smell | 3 | 3 | 3 | 3 |

TABLE 6-continued

Fecal score for healthy dogs

|  | Day 1 | Day 7 | Day 15 | Day 30 |
|---|---|---|---|---|
| Gut rumbling | – | – | – | – |
| Flatulence | – | – | – | – |
| 08-C | | | | |
| Stool Consistency | 4 | 3 | 3 | 3 |
| Stool Volume | 3 | 2 | 2 | 2 |
| Stool Smell | 3 | 3 | 3 | 3 |
| Gut rumbling | – | – | – | – |
| Flatulence | – | – | – | – |

TABLE 7

Fecal score for dogs with dysbiosis

|  | Day 1 | Day 7 | Day 15 | Day 30 |
|---|---|---|---|---|
| 09-B | | | | |
| Stool Consistency | 3 | 5 | 5 | 5 |
| Stool Volume | 3 | 3 | 3 | 3 |
| Stool Smell | 3 | 2 | 2 | 2 |
| Gut rumbling | – | – | – | – |
| Flatulence | YES | – | YES | – |
| 10-Y | | | | |
| Stool Consistency | 7 | 7 | 7 | 5 |
| Stool Volume | 4 | 4 | 4 | 4 |
| Stool Smell | 3 | 2 | 2 | 2 |
| Gut rumbling | – | – | – | – |
| Flatulence | – | – | – | – |
| 11-L | | | | |
| Stool Consistency | 6 | 6 | 5 | 4 |
| Stool Volume | 4 | 4 | 4 | 4 |
| Stool Smell | 3 | 3 | 2 | 2 |
| Gut rumbling | – | – | – | – |
| Flatulence | – | – | – | – |
| 12-D | | | | |
| Stool Consistency | 6 | 5 | 4 | 4 |
| Stool Volume | 3 | 3 | 3 | 3 |
| Stool Smell | 3 | 2 | 2 | 2 |
| Gut rumbling | – | – | – | – |
| Flatulence | – | – | – | – |
| 13-U | | | | |
| Stool Consistency | 6 | 5 | 5 | 4 |
| Stool Volume | 3 | 3 | 3 | 3 |
| Stool Smell | 3 | 3 | 3 | 3 |
| Gut rumbling | – | – | – | – |
| Flatulence | – | – | – | – |
| 14-M | | | | |
| Stool Consistency | 4 | 5 | 5 | 5 |
| Stool Volume | 3 | 3 | 2+ | 2+ |
| Stool Smell | 3 | 3+ | 4 | 3 |
| Gut rumbling | – | – | – | – |
| Flatulence | – | – | – | – |

Digestibility

Figure 2:
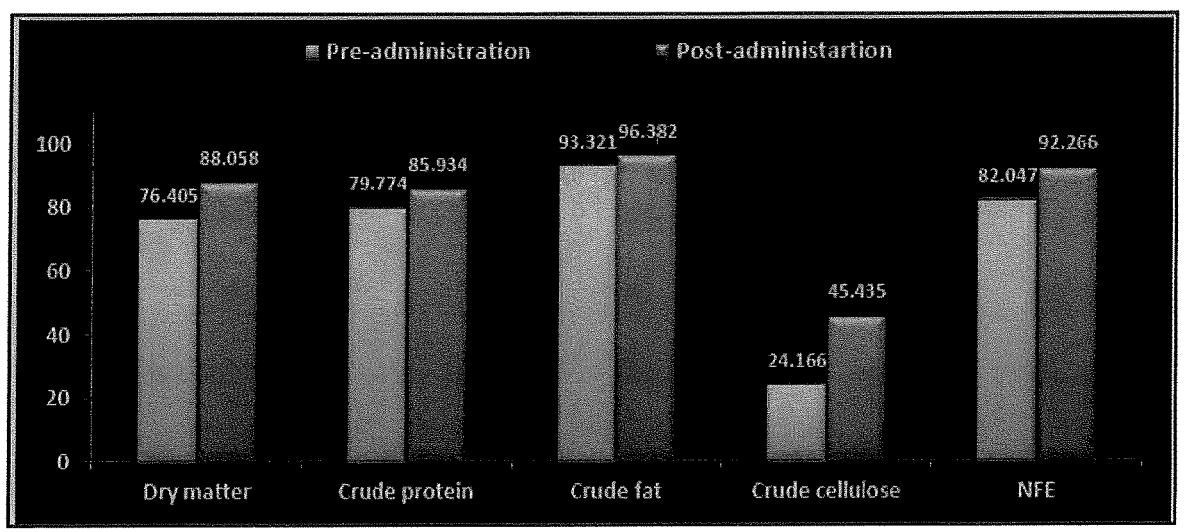
FIG. 2 is a chart showing average digestibility parameters of dry matter, crude protein, crude fat, crude cellulose, and NFE, pre-and post-administration of a probiotic composition of this invention, in healthy dogs.

The study of the digestibility of feedstuffs by measuring the apparent digestibility coefficients shows an important improvement of digestibility of all the studied components (dry matter, crude fat, crude cellulose and NFE) with the exception of crude protein where the values decreased in one case (Dog 02-H) (See Table 8, FIG. 2). The increase of digestibility is statistically important ($p<0.001$) for dry matter, crude protein, and NFE.

TABLE 8

Evolution of digestibility (%) - healthy dogs

| Patient code | Dry matter*** | | Crude protein*** | | Crude fat | | Crude cellulose | | NFE*** | |
|---|---|---|---|---|---|---|---|---|---|---|
|  | Pre-A | Post-A | Pre-A | Post-A | Pre-A | Post-A | Pre-A | Post-A | Pre-A | Post-A |
| 01 - K | 80.959 | 89.588 | 88.305 | 92.623 | 97.638 | 98.637 | 22.945 | 42.273 | 80.666 | 90.051 |
| 02 - H | 77.621 | 85.146 | 84.233 | 75.070 | 90.524 | 91.628 | 23.252 | 34.004 | 81.658 | 89.990 |
| 03 - L | 77.560 | 88.763 | 78.541 | 87.676 | 92.957 | 96.630 | 24.431 | 48.633 | 85.315 | 94.059 |
| 04 - N | 76.345 | 88.190 | 77.346 | 87.461 | 94.310 | 97.851 | 24.367 | 49.539 | 83.915 | 93.142 |
| 05 - D | 69.541 | 88.605 | 70.443 | 86.840 | 91.175 | 97.165 | 25.834 | 52.727 | 78.680 | 94.089 |
| Average | 76.405 | 88.058 | 79.774 | 85.934 | 93.321 | 96.382 | 24.166 | 45.435 | 82.047 | 92.266 |
| St. dev | 4.203 | 1.705 | 6.840 | 6.499 | 2.836 | 2.762 | 1.142 | 7.432 | 2.625 | 2.085 |

***$p < 0.001$ - Extremely significant

Hematology

The hematological parameters for dogs are quite heterogeneous but are always in the normal range of values for dogs. Nevertheless, we observe a slight increase in hemoglobin (Hb), mean corpuscular hemoglobin (MCH), and mean corpuscular hemoglobin concentration (MCHC) (See Tables 9 and 10).

Leucocyte values before and after treatment with a probiotic composition of this invention presented heterogenous results but were in the normal range of values for dogs. Eosinophil values tended to slightly increase in most of the dogs after treatment. Neutrophils, basophils, monocytes, and lymphocytes increased or decreased according to the individual dog (See Tables 11 and 12). Individual and average variations were not considered as having pathological connotations.

A particular situation was observed in dogs with dysbiosis, where eosinophil averages had a small tendency to increase. This was shown by the 14-M patient who had eosinophilia after administration (30%). This value correlated with the diagnosis of ancylostomiasis that was not evidenced ante-administration because of the biological cycle of the parasite (*Ancylostoma coninum*).

TABLE 9

Evolution of erythrocyte parameters - healthy dogs

| Patient Code | HCT (37-55%) | | HGB (12-18 g/dL) | | RBC (5.5-8.5 T/L) | | MCV (60-77 fL) | | MCH (19.5-24.5 pg) | | MCHC (32-36 g/dL) | |
|---|---|---|---|---|---|---|---|---|---|---|---|---|
| | Pre-A | Post-A | Pre-A | Post-A | Pre-A | Post-A | Pre-A | Post-A | Pre-A | Post-A | Pre-A | Post-A |
| 01 - K | 46.74 | 47.01 | 21.30 | 21.70 | 7.11 | 7.13 | 66.00 | 66.00 | 30.00 | 30.50 | 45.60 | 46.20 |
| 02 - H | 45.25 | 42.71 | 21.40 | 21.70 | 7.22 | 6.84 | 63.00 | 62.00 | 29.60 | 31.70 | 47.20 | 50.80 |
| 06 - A | 38.36 | 37.71 | 18.20 | 16.10 | 7.47 | 7.48 | 51.00 | 50.00 | 24.40 | 21.50 | 47.50 | 42.60 |
| 07 - I | 36.78 | 38.88 | 15.10 | 15.80 | 6.09 | 6.45 | 60.00 | 60.00 | 24.70 | 24.40 | 41.00 | 40.60 |
| 08 - C | 40.19 | 36.38 | 18.80 | 15.40 | 7.64 | 6.83 | 53.00 | 53.00 | 24.70 | 22.50 | 46.90 | 42.20 |
| Average | 41.46 | 40.54 | 18.96 | 18.14 | 7.11 | 6.95 | 58.60 | 58.20 | 26.68 | 26.12 | 45.64 | 44.48 |
| St. dev. | 4.34 | 4.32 | 2.59 | 3.26 | 0.60 | 0.38 | 6.43 | 6.57 | 2.85 | 4.68 | 2.69 | 4.08 |

TABLE 10

Evolution of erythrocyte parameters - dogs with dysbiosis

| Patient Code | HCT (37-55%) | | HGB (12-18 g/dL) | | RBC (5.5-8.5 T/L) | | MCV (60-77 fL) | | MCH (19.5-24.5 pg) | | MCHC (32-36 g/dL) | |
|---|---|---|---|---|---|---|---|---|---|---|---|---|
| | Pre-A | Post-A | Pre-A | Post-A | Pre-A | Post-A | Pre-A | Post-A | Pre-A | Post-A | Pre-A | Post-A |
| 09 - B | 38.93 | 42.11 | 18.20 | 19.80 | 5.75 | 6.63 | 68.00 | 64.00 | 31.70 | 29.90 | 46.90 | 47.10 |
| 10 - Y | 43.28 | 39.63 | 20.50 | 18.50 | 8.04 | 7.46 | 54.00 | 53.00 | 25.50 | 24.80 | 47.50 | 46.70 |
| 11 - L | 41.25 | 36.23 | 20.20 | 16.50 | 6.00 | 5.48 | 69.00 | 66.00 | 33.70 | 30.20 | 48.90 | 45.60 |
| 12 - D | 42.76 | 42.31 | 19.10 | 19.30 | 6.59 | 6.88 | 65.00 | 61.00 | 29.00 | 28.10 | 44.70 | 45.70 |
| 13 - U | 42.11 | 36.04 | 18.90 | 16.00 | 6.90 | 5.86 | 63.00 | 61.00 | 27.40 | 22.70 | 45.00 | 44.30 |
| 14 - M | 43.91 | 39.07 | 19.80 | 19.20 | 6.70 | 6.25 | 66.00 | 63.00 | 29.50 | 30.70 | 45.00 | 49.10 |
| Average | 42.04 | 39.23 | 19.45 | 18.22 | 6.66 | 6.43 | 63.83 | 61.33 | 29.47 | 27.73 | 46.33 | 46.42 |
| St. dev. | 1.78 | 2.73 | 0.87 | 1.59 | 0.80 | 0.72 | 5.56 | 4.50 | 2.94 | 3.28 | 1.70 | 1.64 |

TABLE 11

Evolution of leucocyte parameters - healthy dogs

Differential white cell count

| Patient code | WBC (6-17 G/L) | | Neutrophil (58-85%) | | Eosinophil (0-9%) | | Basophil (0-1%) | | Monocyte (2-10%) | | Lymphocyte (8-21%) | |
|---|---|---|---|---|---|---|---|---|---|---|---|---|
| | Pre-A | Post-A | Pre-A | Post-A | Pre-A | Post-A | Pre-A | Post-A | Pre-A | Post-A | Pre-A | Post-A |
| 01 - K | 13.35 | 12.95 | 43.00 | 51.00 | 7.00 | 7.00 | 0.00 | 0.00 | 17.00 | 12.00 | 33.00 | 30.00 |
| 02 - H | 18.80 | 19.69 | 54.00 | 59.00 | 6.00 | 7.00 | 0.00 | 0.00 | 9.00 | 11.00 | 31.00 | 23.00 |
| 06 - A | 14.20 | 15.61 | 61.00 | 73.00 | 4.00 | 5.00 | 0.00 | 0.00 | 15.00 | 8.00 | 20.00 | 14.00 |
| 07 - I | 12.40 | 15.80 | 60.00 | 66.00 | 7.00 | 1.00 | 0.00 | 0.00 | 8.00 | 13.00 | 25.00 | 20.00 |
| 08 - C | 12.40 | 15.80 | 57.00 | 72.00 | 10.00 | 3.00 | 0.00 | 0.00 | 2.00 | 16.00 | 31.00 | 9.00 |
| Average | 14.23 | 15.97 | 55.00 | 64.20 | 6.80 | 4.60 | 0.00 | 0.00 | 10.20 | 12.00 | 28.00 | 19.20 |
| St. dev. | 2.66 | 2.41 | 7.25 | 9.26 | 2.17 | 2.61 | 0.00 | 0.00 | 5.97 | 2.92 | 5.39 | 8.11 |

TABLE 12

Evolution of leukocyte parameters - dogs withy dysbiosis

| Patient code | WBC (6-17 G/L) | | Differential white cell count | | | | | | | | | |
|---|---|---|---|---|---|---|---|---|---|---|---|---|
| | | | Neutrophil (58-85%) | | Eosinophil (0-9%) | | Basophil (0-1%) | | Monocyte (2-10%) | | Lymphocyte (8-21%) | |
| | Pre-A | Post-A | Pre-A | Post-A | Pre-A | Post-A | Pre-A | Post-A | Pre-A | Post-A | Pre-A | Post-A |
| 09 - B | 12.17 | 9.31 | 38.00 | 64.00 | 7.00 | 2.00 | 0.00 | 1.00 | 8.00 | 14.00 | 47.00 | 19.00 |
| 10 - Y | 6.83 | 7.08 | 60.00 | 68.00 | 5.00 | 1.00 | 0.00 | 0.00 | 14.00 | 13.00 | 21.00 | 18.00 |
| 11 - L | 10.58 | 12.59 | 48.00 | 62.00 | 10.00 | 4.00 | 0.00 | 0.00 | 9.00 | 12.00 | 33.00 | 22.00 |
| 12 - D | 17.13 | 14.97 | 63.00 | 75.00 | 4.00 | 11.00 | 0.00 | 0.00 | 11.00 | 4.00 | 22.00 | 10.00 |
| 13 - U | 10.22 | 12.27 | 64.00 | 71.00 | 5.00 | 9.00 | 0.00 | 0.00 | 9.00 | 10.00 | 22.00 | 10.00 |
| 14 - M | 12.13 | 15.22 | 63.00 | 40.00 | 6.00 | 30.00 | 0.00 | 0.00 | 18.00 | 13.00 | 13.00 | 17.00 |
| Average | 11.51 | 11.91 | 56.00 | 63.33 | 6.17 | 9.50 | 0.00 | 0.17 | 11.50 | 11.00 | 26.33 | 16.00 |
| St. dev. | 3.37 | 3.19 | 10.64 | 12.36 | 2.14 | 10.78 | 0.00 | 0.41 | 3.83 | 3.69 | 11.96 | 4.94 |

Biochemistry

An investigation into biochemical parameters indicated the health of different systems and organs, and also indicated how the probiotic composition acted on the dogs (Table 13).

TABLE 13

Investigated biochemical parameters

| No | Parameter | Indications |
|---|---|---|
| 1 | Alanine aminotransferase (ALT) | Liver diseases, including viral hepatitis and cirrhosis; heart diseases. |
| 2 | Albumin | Liver and kidney diseases. |
| 3 | Alkaline phosphatase | Liver, bone, parathyroid, and intestinal diseases. |
| 4 | Amylase | Kidney and pancreatic disease. |
| 5 | Calcium | Parathyroid, bone and chronic renal disease; tetany. |
| 6 | Creatinine | Renal disease. |
| 7 | Globulin | Globulin concentration will increase with dehydration and should also increase with antigenic stimulation. |
| 8 | Glucose | Diabetes, hyperglycemia, hypoglycemia, diabetes and liver disease. |
| 9 | Phosphorus | Kidney disease, hypoparathyroidism and nutritional disorders. |
| 10 | Potassium | Malnutrion and renal disease. This electrolyte is used to diagnose the causes of vomiting, diarrhea and cardiac symptoms. |
| 11 | Sodium | Dehydration and diabetes. This electrolyte is used to diagnose the causes of vomiting, diarrhea and cardiac symptoms. |
| 12 | Total bilirubin | Hepatic disorders. |
| 13 | Total protein | Dehydration, kidney, liver disease, metabolic and nutritional disorders. |
| 14 | Blood Urea Nitrogen | Liver and kidney diseases. |

Tables 14, 15, 16, and 17 present results for the biochemical parameters before and after treatment with a probiotic composition of the present invention for all cases.

The biochemical parameters for dogs were heterogeneous but always in the normal range of values for dogs. Biochemical results are correlated with clinical observations recorded ante-and post-administration.

The 07-I patient, in the healthy group of dogs, showed high levels of ALT and potassium pre-administration. This increase was not correlated with alterations of other biochemical, hematological, or clinical parameters, so the dog remained in the study. The post-administration ALT level was within the physiological limits of the species, and potassium continued to present with higher levels.

TABLE 14

Evolution of biochemical parameters - healthy dogs

| Patient code | ALT (10-118 U/L) | | ALB (25-44 g/L) | | ALP (20-150 U/L) | | Amylase (200-1200 U/L) | | Creatinine (27-124 umol/L) | |
|---|---|---|---|---|---|---|---|---|---|---|
| | Pre-A | Post-A | Pre-A | Post-A | Pre-A | Post-A | Pre-A | Post-A | Pre-A | Post-A |
| 01 - K | 41 | 45 | 36 | 39 | 38 | 33 | 520 | 526 | 132 | 102 |
| 02 - H | 51 | 58 | 41 | 39 | 46 | 39 | 499 | 400 | 93 | 84 |
| 06 - A | 64 | 35 | 39 | 36 | 37 | 42 | 397 | 438 | 49 | 62 |
| 07 - I | 476 | 50 | 41 | 39 | 35 | 37 | 483 | 405 | 52 | 44 |
| 08 - C | 59 | 33 | 35 | 29 | 31 | 60 | 552 | 711 | 114 | 84 |
| Average | 138.20 | 44.40 | 38.40 | 36.40 | 37.40 | 42.20 | 190.20 | 496.00 | 88.00 | 75.20 |
| St. dev. | 189.04 | 10.45 | 2.79 | 4.34 | 5.50 | 10.47 | 58.14 | 130.37 | 36.93 | 22.48 |

| Patient code | Globulin (23-52 g/L) | | Glucose (3.3-6.1 mmol/L) | | Total Bilirubin (2-10 umol/L) | | Total protein (54-82 g/L) | | Blood Urea Nitrogen (BUN) (2.5-8.9 mmol/L) | |
|---|---|---|---|---|---|---|---|---|---|---|
| | Pre-A | Post-A | Pre-A | Post-A | Pre-A | Post-A | Pre-A | Post-A | Pre-A | Post-A |
| 01 - K | 30 | 24 | 4 | 4 | 5 | 7 | 65 | 63 | 7.1 | 10.3 |
| 02 - H | 25 | 23 | 5.1 | 4.9 | 5 | 4 | 65 | 63 | 8.1 | 7.9 |
| 06 - A | 26 | 32 | 4.3 | 3.5 | 4 | 5 | 68 | 67 | 2.6 | 4.7 |
| 07 - I | 24 | 26 | 4 | 3.5 | 4 | 5 | 65 | 55 | 4.2 | 3.8 |
| 08 - C | 22 | 28 | 3.9 | 4.1 | 4 | 5 | 57 | 57 | 4.9 | 2.8 |
| Average | 25.40 | 26.60 | 4.26 | 4.00 | 4.40 | 5.20 | 64.00 | 63.00 | 5.38 | 5.90 |
| St. dev. | 2.97 | 3.58 | 0.49 | 0.57 | 0.55 | 1.10 | 3.94 | 3.74 | 2.22 | 3.12 |

TABLE 15

Evolution of biochemical parameters - dogs with dysbiosis

| Patient code | ALT (10-118 U/L) | | ALB (25-44 g/L) | | ALP (20-150 U/L) | | Amylase (200-1200 U/L) | | Creatinine (27-124 umol/L) | |
|---|---|---|---|---|---|---|---|---|---|---|
| | Pre-A | Post-A | Pre-A | Post-A | Pre-A | Post-A | Pre-A | Post-A | Pre-A | Post-A |
| 09 - B | 38 | 52 | 35 | 33 | 135 | 121 | 648 | 641 | 45 | 65 |
| 10 - Y | 86 | 108 | 39 | 37 | 81 | 77 | 443 | 310 | 67 | 60 |
| 11 - L | 41 | 37 | 38 | 35 | 52 | 39 | 472 | 600 | 65 | 61 |
| 12 - D | 52 | 54 | 36 | 35 | 51 | 54 | 612 | 741 | 41 | 63 |
| 13 - U | 35 | 30 | 33 | 31 | 42 | 38 | 986 | 914 | 162 | 117 |
| 14 - M | 33 | 38 | 39 | 39 | 24 | 28 | 473 | 542 | 109 | 97 |
| Average | 47.50 | 53.17 | 36.67 | 35.00 | 64.17 | 59.50 | 605.67 | 624.67 | 81.50 | 77.17 |
| St. dev. | 20.01 | 28.41 | 2.42 | 2.83 | 39.31 | 34.62 | 204.16 | 201.98 | 46.24 | 24.02 |

| Patient code | Globulin (23-52 g/L) | | Glucose (3.3-6.1 mmol/L) | | Total Bilirubin (2-10 umol/L) | | Total protein (54-82 g/L) | | Blood Urea Nitrogen (BUN) (2.5-8.9 mmol/L) | |
|---|---|---|---|---|---|---|---|---|---|---|
| | Pre-A | Post-A | Pre-A | Post-A | Pre-A | Post-A | Pre-A | Post-A | Pre-A | Post-A |
| 09 - B | 21 | 21 | 5.6 | 5.6 | 5 | 6 | 56 | 54 | 4.5 | 5.1 |
| 10 - Y | 25 | 25 | 5.5 | 5.6 | 4 | 5 | 64 | 62 | 2.9 | 3.0 |
| 11 - L | 25 | 29 | 5.8 | 6.3 | 4 | 5 | 63 | 64 | 5.7 | 5 |
| 12 - D | 18 | 22 | 4.7 | 4.9 | 3 | 5 | 55 | 57 | 4.3 | 3.8 |
| 13 - U | 33 | 33 | 3.6 | 4 | 5 | 5 | 66 | 64 | 7.7 | 7 |
| 14 - M | 31 | 28 | 4.4 | 3.9 | 5 | 5 | 70 | 67 | 7.9 | 7.2 |
| Average | 25.50 | 26.33 | 4.93 | 5.05 | 4.33 | 5.17 | 62.33 | 61.33 | 5.50 | 5.18 |
| St. dev. | 5.72 | 4.55 | 0.85 | 0.95 | 0.82 | 0.41 | 5.82 | 4.89 | 1.99 | 1.68 |

TABLE 16

Evolution of ionogram - healthy dogs

| Patient Code | Calcium (2.15-2.95 mmol/L) | | Phosphorus (0.94-2.13 mmol/L) | | Potassium (3.7-5.8 mmol/L) | | Sodium (138-160 mmol/L) | |
|---|---|---|---|---|---|---|---|---|
| | Pre-A | Post-A | Pre-A | Post-A | Pre-A | Post-A | Pre-A | Post-A |
| 01 - K | 2.55 | 2.65 | 2.10 | 1.99 | 4.7 | 5.2 | 146 | 142 |
| 02 - H | 2.64 | 2.59 | 1.53 | 1.77 | 4.7 | 5.1 | 145 | 142 |
| 06 - A | 2.40 | 2.27 | 1.40 | 1.58 | 4.6 | 4.7 | 145 | 143 |
| 07 - I | 2.49 | 2.48 | 1.20 | 1.18 | 8.5 | 12 | 147 | 146 |
| 08 - C | 2.33 | 2.03 | 1.83 | 1.57 | 5.2 | 4.7 | 149 | 139 |
| Average | 2.48 | 2.40 | 1.61 | 1.62 | 5.54 | 6.34 | 146.40 | 142.40 |
| St. dev | 0.12 | 0.25 | 0.36 | 0.30 | 1.67 | 3.17 | 1.67 | 2.51 |

TABLE 17

Evolution of ionogram - dogs with dysbiosis

| Patient Code | Calcium (2.15-2.95 mmol/L) | | Phosphorus (0.94-2.13 mmol/L) | | Potassium (3.7-5.8 mmol/L) | | Sodium (138-160 mmol/L) | |
|---|---|---|---|---|---|---|---|---|
| | Pre-A | Post-A | Pre-A | Post-A | Pre-A | Post-A | Pre-A | Post-A |
| 09 - B | 2.77 | 2.71 | 3.08 | 2.40 | 4.9 | 4.3 | 145 | 145 |
| 10 - Y | 2.55 | 2.59 | 1.46 | 1.33 | 3.9 | 4.0 | 146 | 149 |
| 11 - L | 2.67 | 2.66 | 1.75 | 1.37 | 4.6 | 4.2 | 149 | 143 |
| 12 - D | 2.13 | 2.27 | 2.09 | 1.88 | 4.9 | 4.7 | 144 | 147 |
| 13 - U | 2.57 | 2.39 | 1.19 | 1.28 | 4.7 | 4.6 | 146 | 141 |
| 14 - M | 2.70 | 2.63 | 1.88 | 1.77 | 4.9 | 4.7 | 145 | 145 |
| Average | 2.57 | 2.54 | 1.91 | 1.67 | 4.65 | 4.42 | 145.83 | 145 |
| St. dev | 0.23 | 0.17 | 0.66 | 0.43 | 0.39 | 0.29 | 1.72 | 2.83 |

Endotoxemia

A. Healthy Dogs

Figure 34:
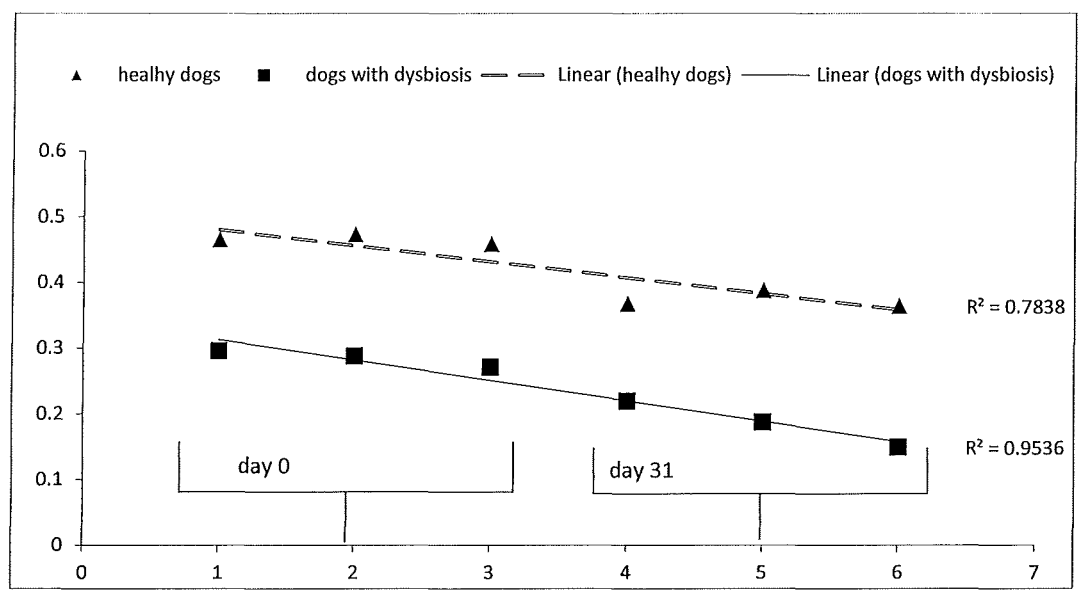
FIG. 34 is a chart showing changes in the level of endotoxemia (EU/ml) in healthy dogs and dogs with dysbiosis, pre-(day 0) and post-(day 31) administration of a probiotic composition of this invention.

Before the administration of the probiotic composition, an increase in the mean endotoxin level 6 hours post-meal as compared with pre-meal mean levels was observed (pre-meal, 0.465±0.113 EU/ml; 6 hours post meal, 0.473±0.172 EU/ml). The same dynamic was observed after completion of 30 days of probiotic administration, with endotoxin levels increasing from 0.3677±0.2266 EU/ml (pre-meal) to 0.388±0.233 EU/ml (6 hours post-meal) (See Table 19, showing changes in endotoxemia levels in healthy dogs and dogs with dysbiosis, and FIG. 34, showing changes in the level of endotoxemia (EU/ml) in healthy dogs and dogs with dybiosis (pre-and post-probiotic treatment)). These differences were not statistically significant because of the high level of variation between individual dogs.

Figure 3:
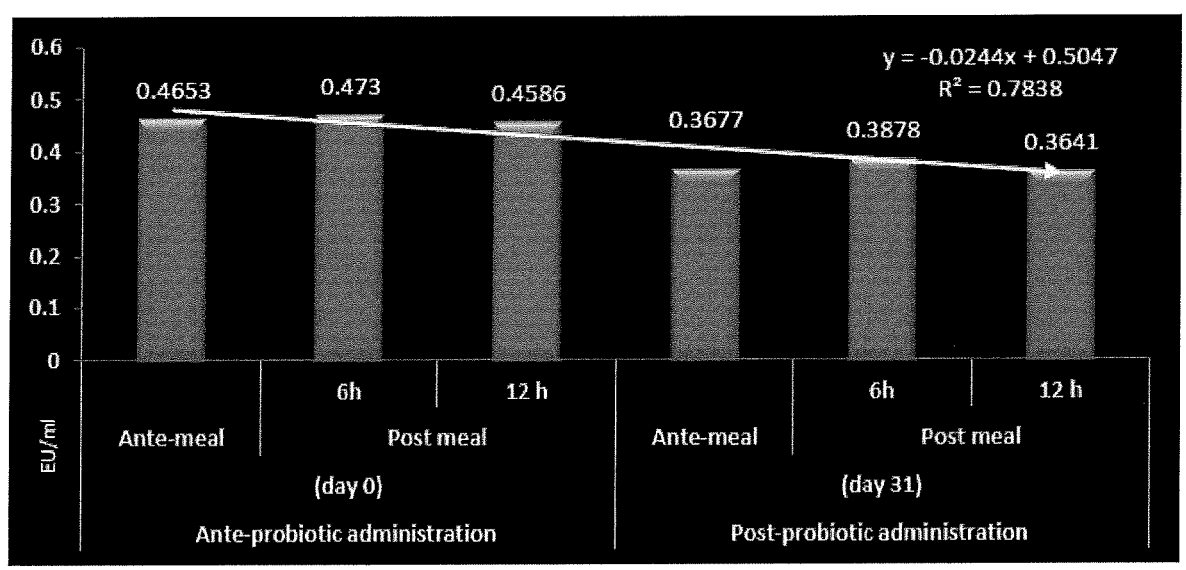
FIG. 3 is a chart showing averages and a trend line relating to endotoxemia in healthy dogs before and after administration of a probiotic composition according to this invention.
Figure 4:
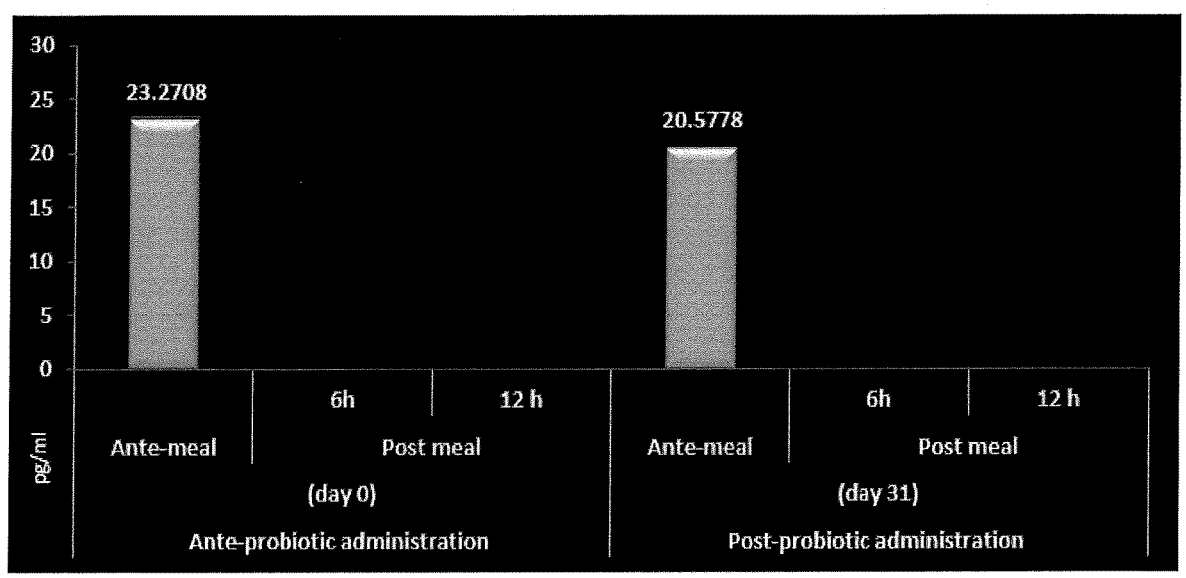
FIG. 4 is a chart showing average CD14 values in healthy dogs before and after administration of a probiotic composition of this invention.
Figure 35:
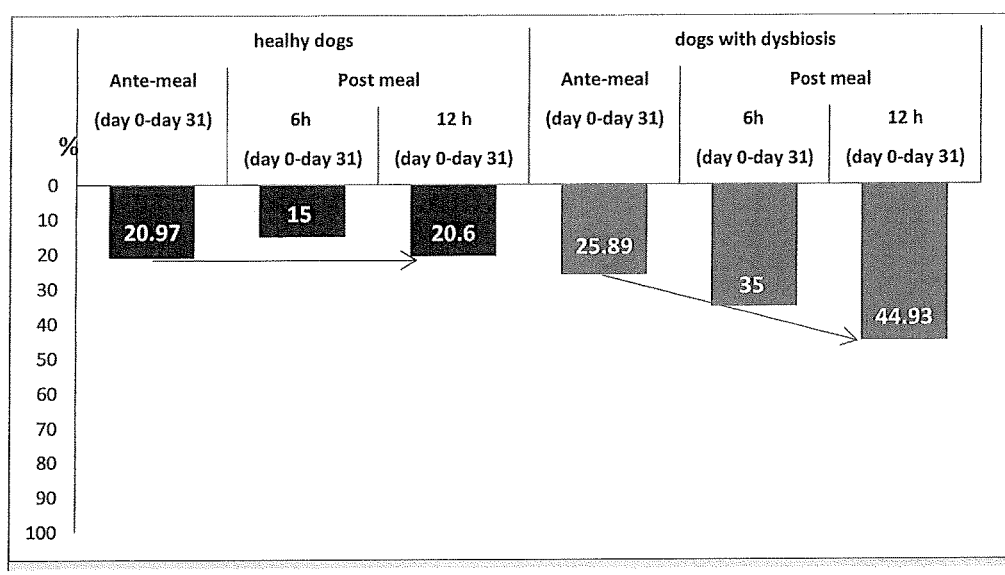
FIG. 35 is a chart showing the percentage decrease in endotoxin levels from day 0 to day 31 in healthy dogs and dogs with dysbiosis, before (ante-) and after (post-) meals, according to the present invention.

Importantly, endotoxin levels decreased after 30 days of administration of the probiotic composition (See Table 18 and FIG. 3). The average percentage decreases in endotoxin levels (EU/ml) from day 0 to day 31 in healthy dogs (pre-and post-biotic treatment) are shown in FIG. 35, and were as follows: pre-meal: 20.97%; 6 hours post-meal: 15%; 12 hours post-meal: 20.6%. In direct correlation with the trend of decreasing levels of endotoxin is the evolution of CD14 (Table 20; FIG. 4). The correlation coefficient of the two parameters (r=0.8452, $R^2$=0.744) indicate statistical significance (p=0.05).

TABLE 18

Evolution of endotoxemia (EU/ml) - healthy dogs

| Patient code | Ante-probiotic administration (day 0) | | | Post-probiotic administration (day 31) | | |
|---|---|---|---|---|---|---|
| | Ante-meal | Post meal 6 h | Post meal 12 h | Ante-meal | Post meal 6 h | Post meal 12 h |
| 09 - B | 0.2706 | 0.1872 | 0.1690 | 0.0986 | 0.1799 | 0.1226 |
| 10 - Y | 0.1340 | 0.1497 | 0.0923 | 0.0871 | 0.1080 | 0.1080 |
| 11 - L | 0.5082 | 0.6375 | 0.5124 | 0.6479 | 0.4415 | 0.2643 |
| 12 - D | 0.4269 | 0.2768 | 0.3769 | 0.1648 | 0.0986 | 0.0871 |
| 13 - U | 0.1393 | 0.1888 | 0.2060 | 0.0976 | 0.1080 | 0.1653 |
| 14 - M | 0.2450 | 0.1955 | 0.2435 | 0.4415 | 0.3498 | 0.3686 |
| Average | 0.2958 | 0.2880 | 0.2713 | 0.2192 | 0.1872 | 0.1494 |
| St. dev | 0.1685 | 0.2009 | 0.1703 | 0.2416 | 0.1459 | 0.0703 |

TABLE 19

Change in endotoxemia levels (EU/ml)

| Endotoxemia evaluation moment | Healthy Dogs | | Dogs with Dysbiosis | |
|---|---|---|---|---|
| | Pre-Administration (day 0) | Post-Administration (day 31) | Pre-Administration (day 0) | Post-Administration (day 31) |
| Pre-meal | 0.4653 ± 0.113 | 0.3677 ± 0.226 | 0.2958 ± 0.168 | 0.2192 ± 0.241 |
| Post-meal (6 hours) | 0.4730 ± 0.172 | 0.3878 ± 0.232 | 0.2880 ± 0.200 | 0.1872 ± 0.145 |
| Post-meal (12 hours) | 0.4586 ± 0.149 | 0.3641 ± 0.242 | 0.2713 ± 0.170 | 0.1494 ± 0.070 |

TABLE 20

Evolution of CD14 (pg/ml) - healthy dogs

| | Ante-probiotic administration (day 0) | | | Post-probiotic administration (day 31) | | |
|---|---|---|---|---|---|---|
| | | Post meal | | | Post meal | |
| Patient code | Ante-meal | 6 h | 12 h | Ante-meal | 6 h | 12 h |
| 01 - K | 19.2467 | — | — | 19.5558 | — | — |
| 02 - H | 19.1447 | — | — | 19.8347 | — | — |
| 06 - A | 24.7471 | — | — | 19.5558 | 19.0096 | 18.8421 |
| 07 - I | 31.0407 | — | — | 25.2337 | 30.1738 | 22.3324 |
| 08 - C | 22.1748 | — | — | 18.7092 | 20.0465 | 19.9050 |
| Average | 23.2708 | — | — | 20.5778 | — | — |
| St. dev. | 4.9237 | — | — | 2.6368 | — | — |

Figure 5:
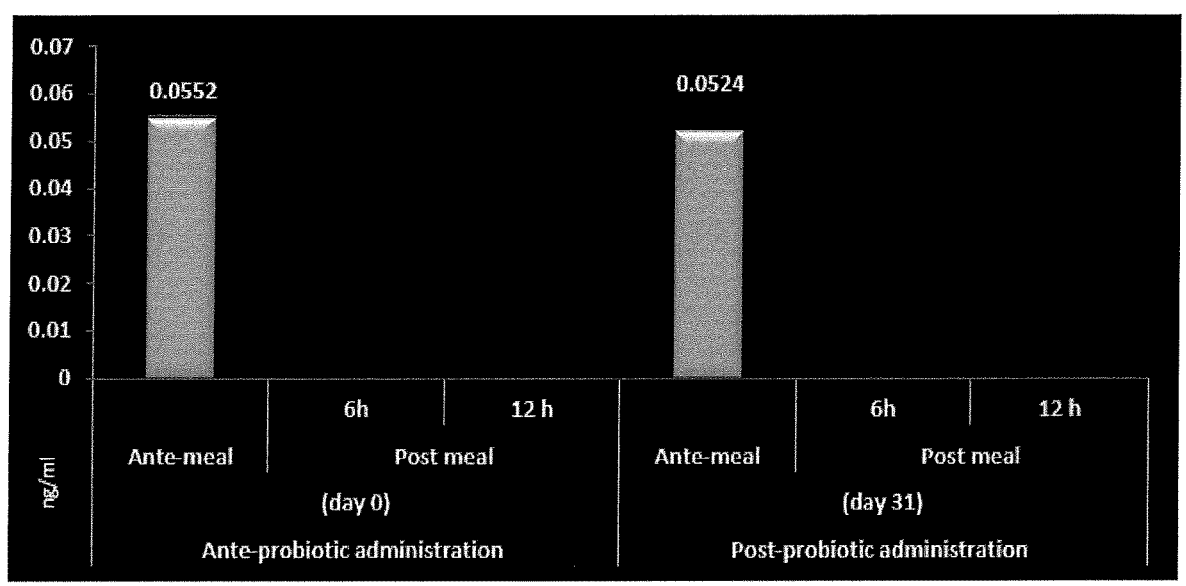
FIG. 5 is a chart showing average IL-1B values in healthy dogs before and after administration of a probiotic composition of this invention.

Regarding the evolution of IL1B levels, values of this parameter remained relatively constant (Table 21, FIG. 5).

TABLE 21

Evolution of IL1B (ng/ml) - healthy dogs

| | Ante-probiotic administration (day 0) | | | Post-probiotic administration (day 31) | | |
|---|---|---|---|---|---|---|
| | | Post meal | | | Post-meal | |
| Patient code | Ante-meal | 6 h | 12 h | Ante-meal | 6 h | 12 h |
| 01 - K | 0.0447 | — | — | 0.322 | — | — |
| 02 - H | 0.0293 | — | — | 0.0534 | — | — |
| 06 - A | 0.0640 | — | — | 0.0463 | 0.0581 | 0.0460 |
| 07 - I | 0.0810 | — | — | 0.0715 | 0.0847 | 0.0665 |
| 08 - C | 0.0571 | — | — | 0.0586 | 0.0506 | 0.0353 |
| Average | 0.0552 | — | — | 0.0524 | — | — |
| St. dev. | 0.0195 | — | — | 0.0146 | — | — |

B. Dogs with Dysbiosis

Figure 6:
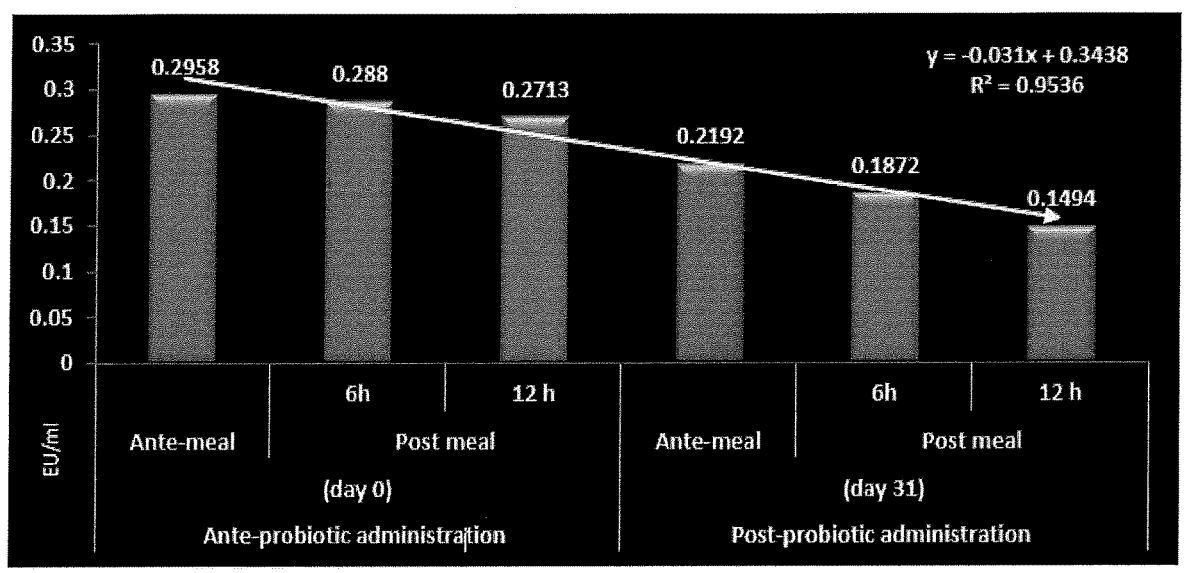
FIG. 6 is a chart showing averages and a trend line of endotoxemia in dogs with dysbiosis before and after administration of a probiotic composition of this invention.

Levels of endotoxemia decreased after completion of treatment with a probiotic composition of this invention (See Table 22, FIGS. 6, 34). The decreasing trend in endotoxemia observed post-probiotic administration had significant progressive dynamics ($R^2$=0.9536) (FIGS. 6, 34). This indicates a significant improvement in intestinal conditions, which would correlate with clinical improvements seen in the dogs from their original diagnosis.

The most important change observed was the decrease in endotoxin levels in dogs with dysbiosis after the completion of 30 days of administration of a probiotic composition of this invention (FIG. 35). The percent decrease from day 0 to day 31 was as follows: pre-meal: 25.89%, 6 hours post-meal: 35%, 12 hours post-meal: 44.93%.

TABLE 22

Evolution of endotoxemia (EU/ml) - dogs with dysbiosis

| | Ante-probiotic administration (day 0) | | | Post-probiotic administration (day 31) | | |
|---|---|---|---|---|---|---|
| | | Post meal | | | Post meal | |
| Patient code | Ante-meal | 6 h | 12 h | Ante-meal | 6 h | 12 h |
| 09 - B | 0.2706 | 0.1872 | 0.1690 | 0.0986 | 0.1799 | 0.1226 |
| 10 - Y | 0.1340 | 0.1497 | 0.0923 | 0.0871 | 0.1080 | 0.1080 |
| 11 - L | 0.5082 | 0.6375 | 0.5124 | 0.6479 | 0.4415 | 0.2643 |
| 12 - D | 0.4269 | 0.2768 | 0.3769 | 0.1648 | 0.0986 | 0.0871 |
| 13 - U | 0.1393 | 0.1888 | 0.2060 | 0.0976 | 0.1080 | 0.1653 |
| 14 - M | 0.2450 | 0.1955 | 0.2435 | 0.4415 | 0.3498 | 0.3686 |
| Average | 0.2958 | 0.2880 | 0.2713 | 0.2192 | 0.1872 | 0.1494 |
| St. dev. | 0.1685 | 0.2009 | 0.1703 | 0.2416 | 0.1459 | 0.0703 |

TABLE 23

Evolution of CD14 (pg/ml) - dogs with dysbiosis

| | Ante-probiotic administration (day 0) | | | Post-probiotic administration (day 31) | | |
|---|---|---|---|---|---|---|
| | | Post meal | | | Post meal | |
| Patient code | Ante-meal | 6 h | 12 h | Ante-meal | 6 h | 12 h |
| 09 - B | 37.6470 | 37.7805 | 35.3852 | 24.0560 | 21.3656 | 20.8426 |
| 10 - Y | 18.9425 | 17.9627 | 19.4178 | 18.5772 | 19.2126 | 19.3834 |
| 11 - L | 22.6509 | 20.8795 | 21.3278 | 20.2605 | 19.9403 | 19.6251 |
| 12 - D | 21.0651 | 22.1356 | 22.3719 | 23.0963 | 21.5555 | 22.4910 |
| 13 - U | 19.8698 | 19.6947 | 19.9756 | 19.5558 | 19.9050 | 20.6955 |
| 14 - M | 21.4413 | 20.7862 | 21.3541 | 21.4413 | 21.3764 | 21.3098 |
| Average | 23.6028 | 23.2065 | 23.3054 | 21.1645 | 20.5592 | 20.7246 |
| St. dev. | 6.9987 | 7.2753 | 6.0119 | 2.1104 | 0.9935 | 1.1389 |

TABLE 24

Evolution of IL1B (ng/ml) - dogs with dysbiosis

| | Ante-probiotic administration (day 0) | | | Post-probiotic administration (day 31) | | |
|---|---|---|---|---|---|---|
| | | Post meal | | | Post meal | |
| Patient code | Ante-meal | 6 h | 12 h | Ante-meal | 6 h | 12 h |
| 09 - B | 0.0736 | 0.0673 | 0.0735 | 0.0293 | 0.0518 | 0.0582 |
| 10 - Y | 0.0292 | 0.028 | 0.0366 | 0.0409 | 0.0418 | 0.0427 |
| 11 - L | 0.0474 | 0.0406 | 0.0369 | 0.0426 | 0.0463 | 0.033 |
| 12 - D | 0.0377 | 0.0384 | 0.0356 | 0.0367 | 0.038 | 0.0351 |
| 13 - U | 0.0367 | 0.0261 | 0.0619 | 0.0392 | 0.0398 | 0.045 |
| 14 - M | 0.0437 | 0.0453 | 0.0468 | 0.0574 | 0.0569 | 0.0575 |
| Average | 0.0447 | 0.0410 | 0.0486 | 0.0410 | 0.0458 | 0.0453 |
| St. dev | 0.0155 | 0.0149 | 0.0158 | 0.0093 | 0.0074 | 0.0107 |

Figure 7:
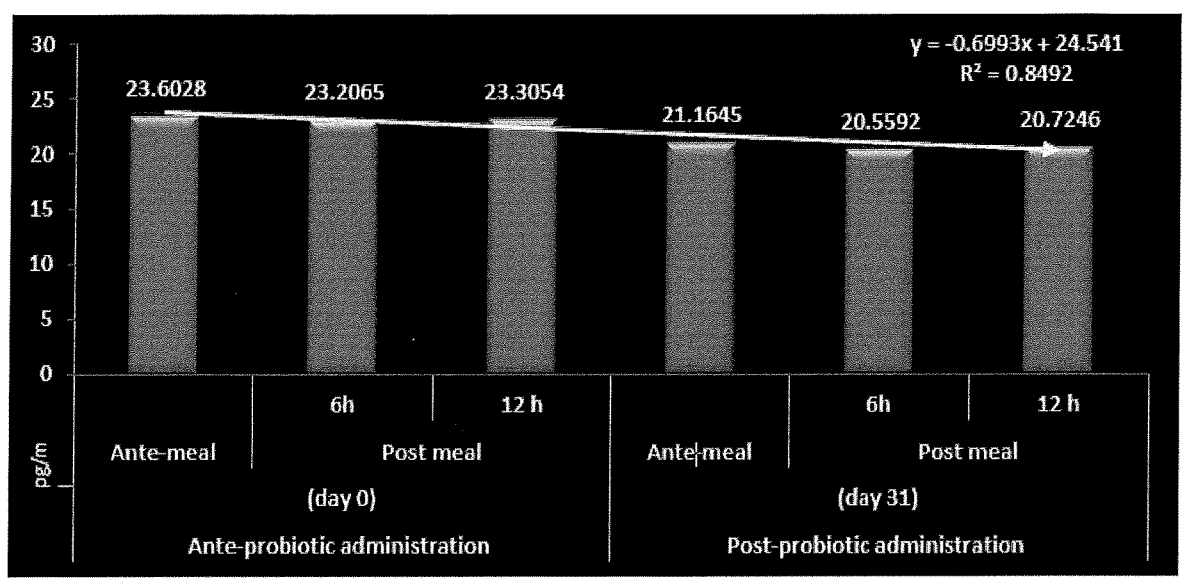
FIG. 7 is a chart showing average CD14 values in dogs with dysbiosis before and after administration of a probiotic composition of this invention.
Figure 8:
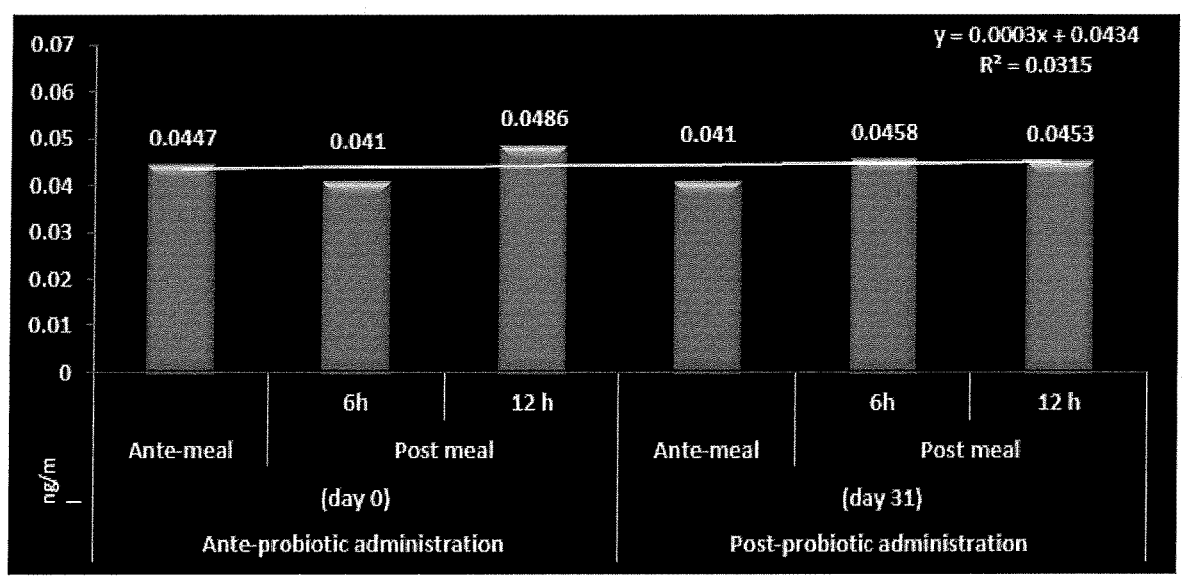
FIG. 8 is a chart showing average IL-1B values in dogs with dysbiosis before and after administration of a probiotic composition of this invention.
Figure 9:
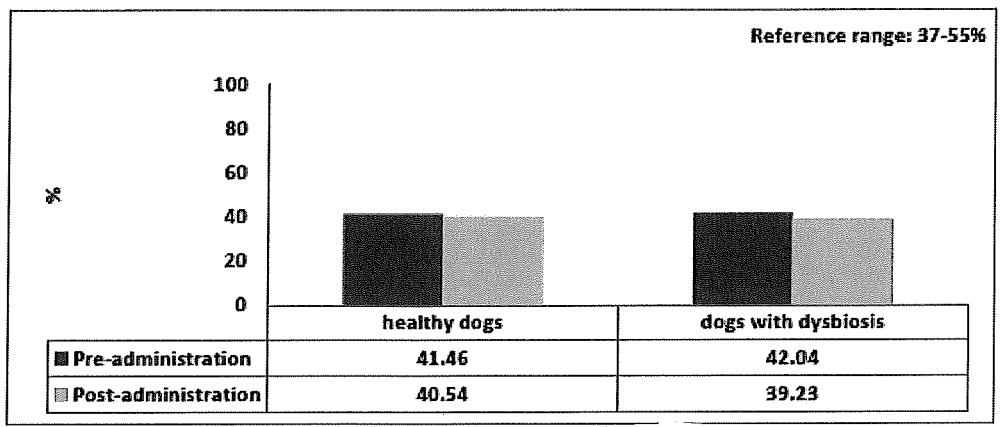
FIG. 9 is a chart showing hematocrit dynamics pre-and post-administration of a probiotic composition of this invention, in healthy dogs and dogs with dysbiosis.
Figure 10:
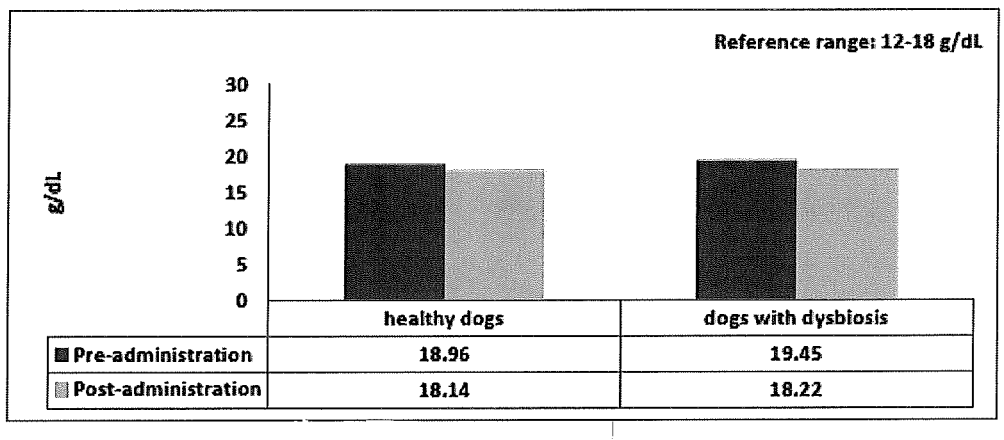
FIG. 10 is a chart showing hemoglobin dynamics pre-and post-administration of a probiotic composition of this invention, in healthy dogs and dogs with dysbiosis.
Figure 11:
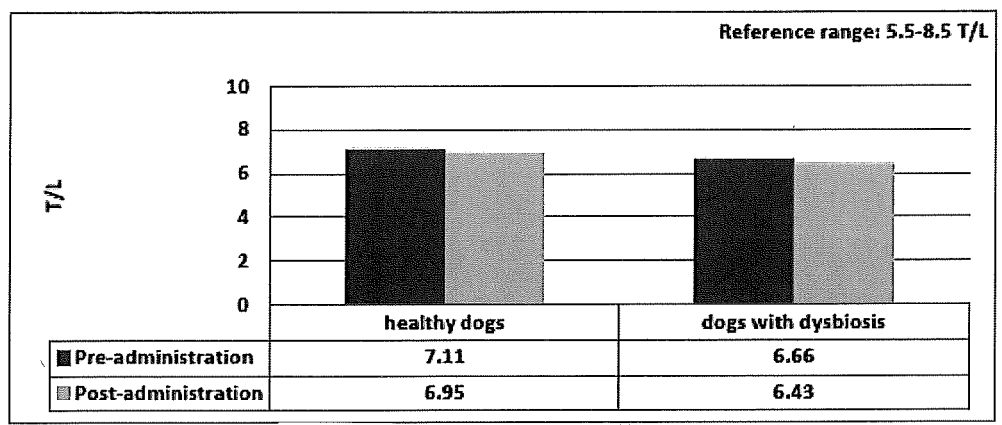
FIG. 11 is a chart showing red blood cell dynamics pre-and post-administration of a probiotic composition of this invention, in healthy dogs and dogs with dysbiosis.
Figure 12:
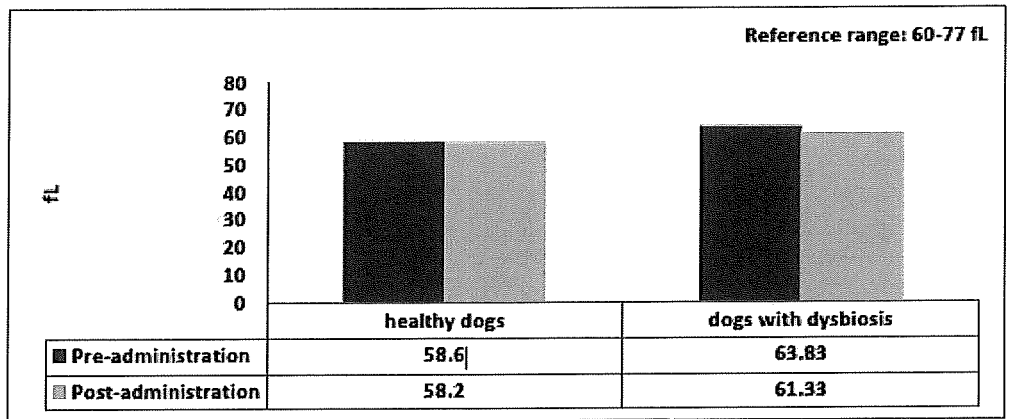
FIG. 12 is a chart showing mean corpuscular volume dynamics pre-and post-administration of a probiotic composition of this invention, in healthy dogs and dogs with dysbiosis.
Figure 13:
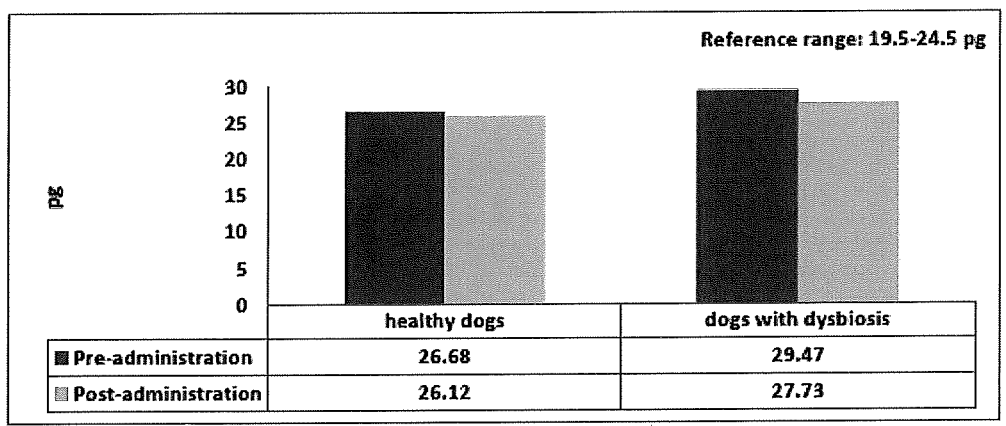
FIG. 13 is a chart showing mean corpuscular hemoglobin dynamics pre-and post-administration of a probiotic composition of this invention, in healthy dogs and dogs with dysbiosis.
Figure 14:
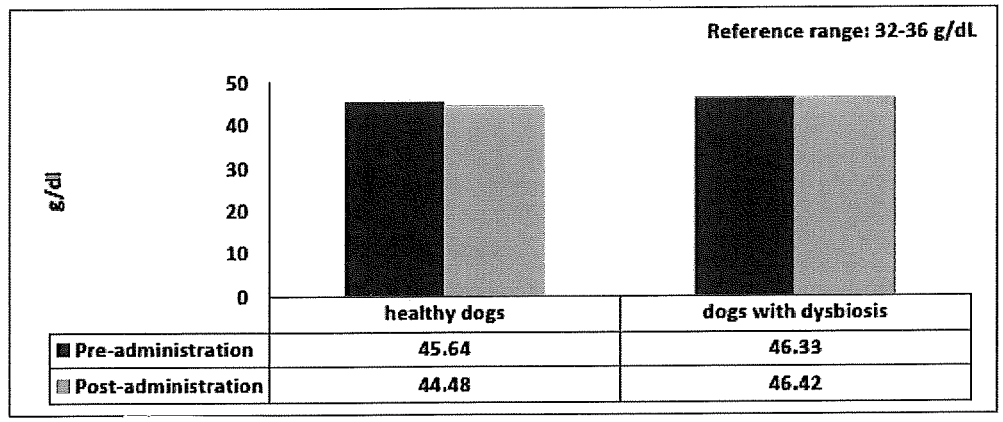
FIG. 14 is a chart showing mean corpuscular hemoglobin concentration dynamics pre-and post-administration of a probiotic composition of this invention, in healthy dogs and dogs with dysbiosis.
Figure 15:
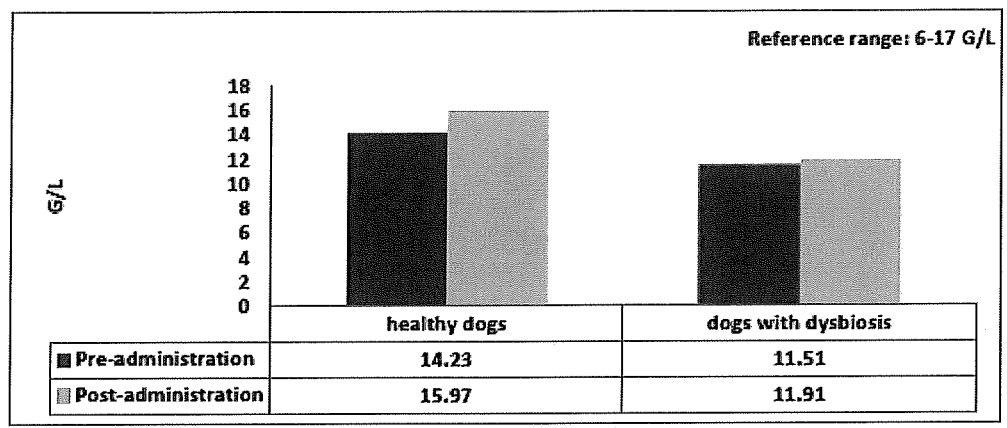
FIG. 15 is a chart showing white blood cell dynamics pre-and post-administration of a probiotic composition of this invention, in healthy dogs and dogs with dysbiosis.
Figure 16:
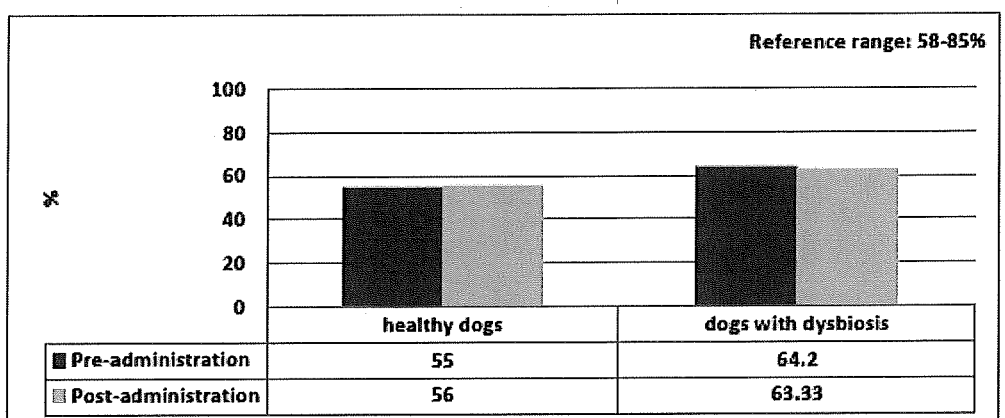
FIG. 16 is a chart showing neutrophil dynamics pre-and post-administration of a probiotic composition of this invention, in healthy dogs and dogs with dysbiosis.
Figure 17:
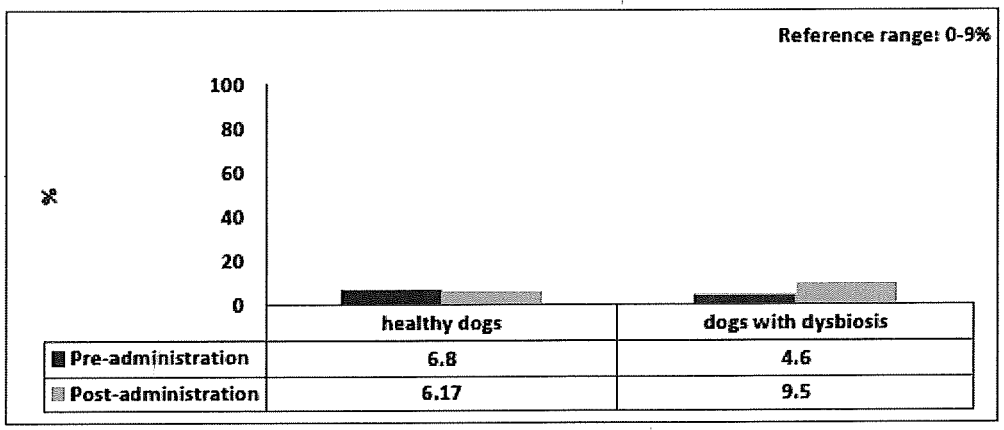
FIG. 17 is a chart showing eosinophil dynamics pre-and post-administration of a probiotic composition of this invention, in healthy dogs and dogs with dysbiosis.
Figure 18:
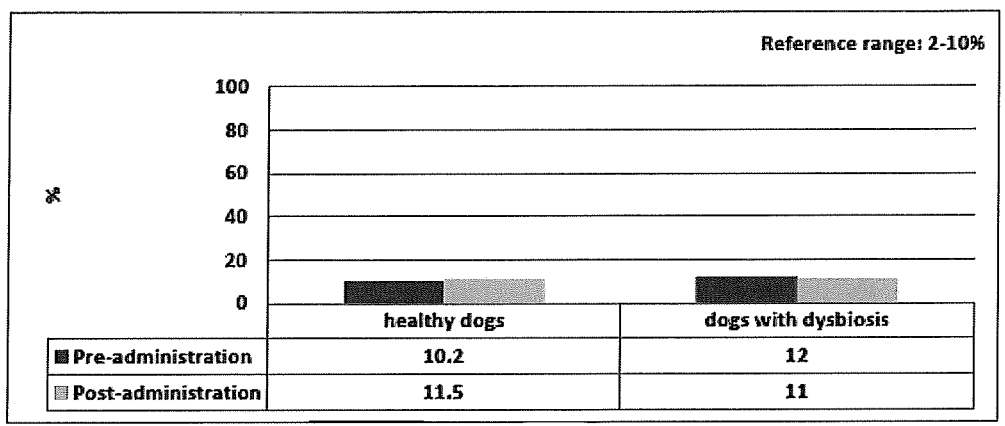
FIG. 18 is a chart showing monocyte dynamics pre-and post-administration of a probiotic composition of this invention, in healthy dogs and dogs with dysbiosis.
Figure 19:
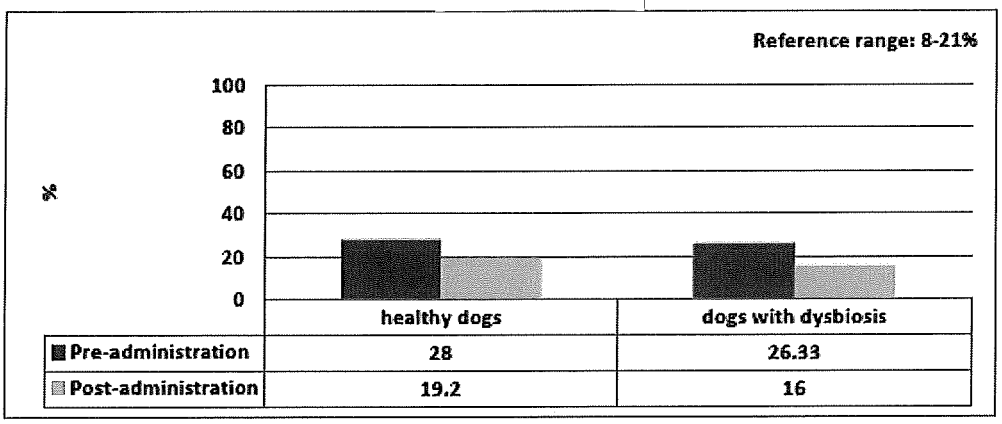
FIG. 19 is a chart showing lymphocyte dynamics pre-and post-administration of a probiotic composition of this invention, in healthy dogs and dogs with dysbiosis.
Figure 20:
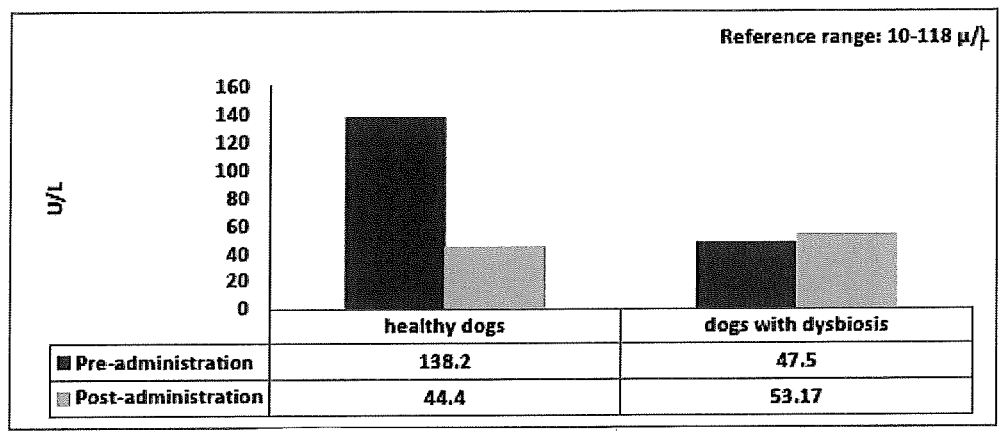
FIG. 20 is a chart showing alanine aminotransferase dynamics pre-and post-administration of a probiotic composition of this invention, in healthy dogs and dogs with dysbiosis.
Figure 21:
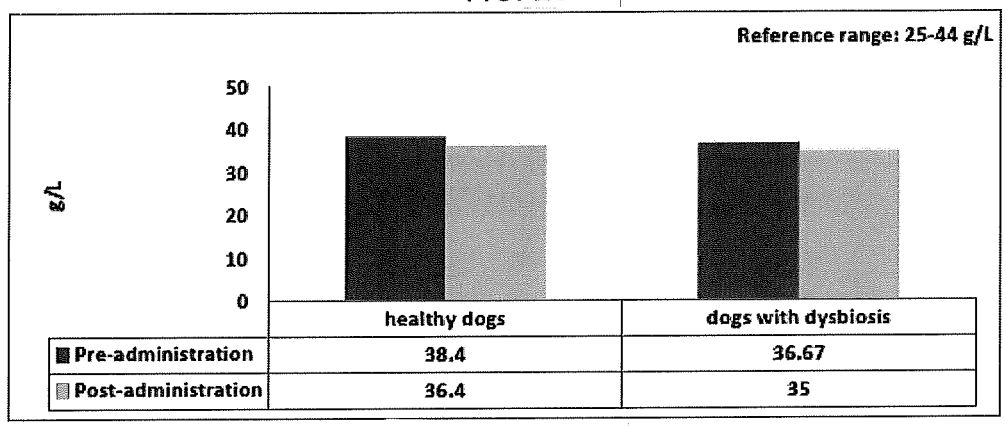
FIG. 21 is a chart showing albumin dynamics pre-and post-administration of a probiotic composition of this invention, in healthy dogs and dogs with dysbiosis.
Figure 22:
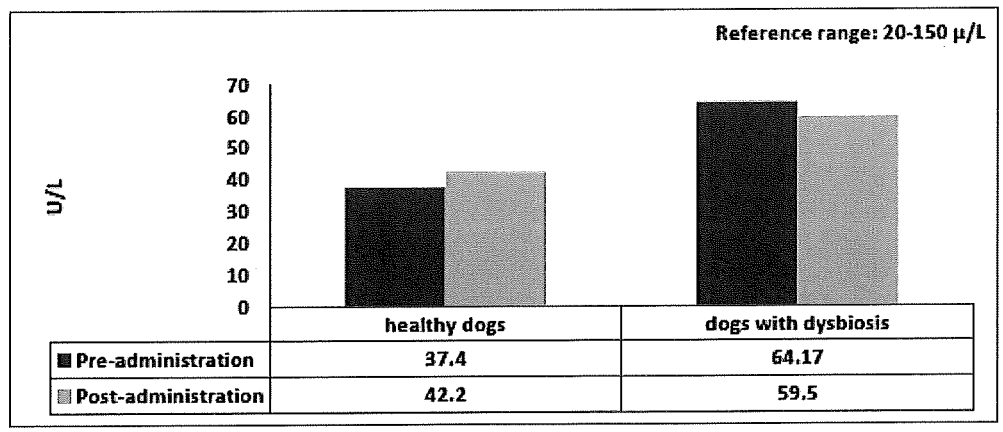
FIG. 22 is a chart showing alkaline phosphatase dynamics pre-and post-administration of a probiotic composition of this invention, in healthy dogs and dogs with dysbiosis.
Figure 23:
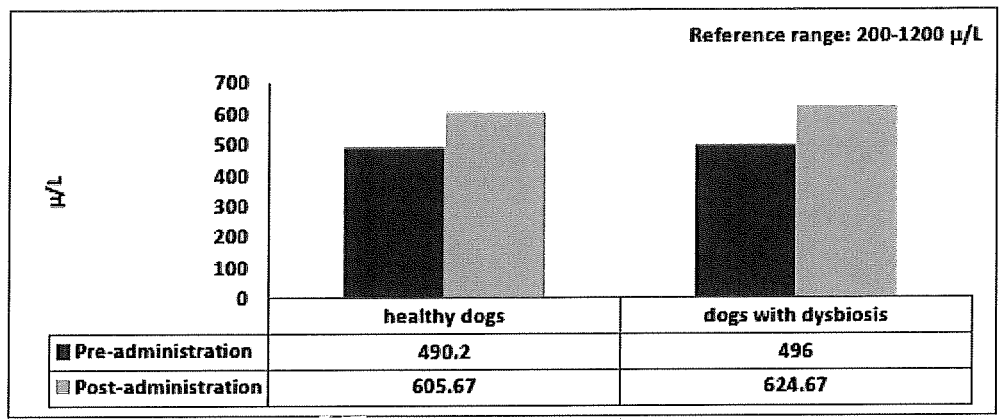
FIG. 23 is a chart showing amylase dynamics pre-and post-administration of a probiotic composition of this invention, in healthy dogs and dogs with dysbiosis.
Figure 24:
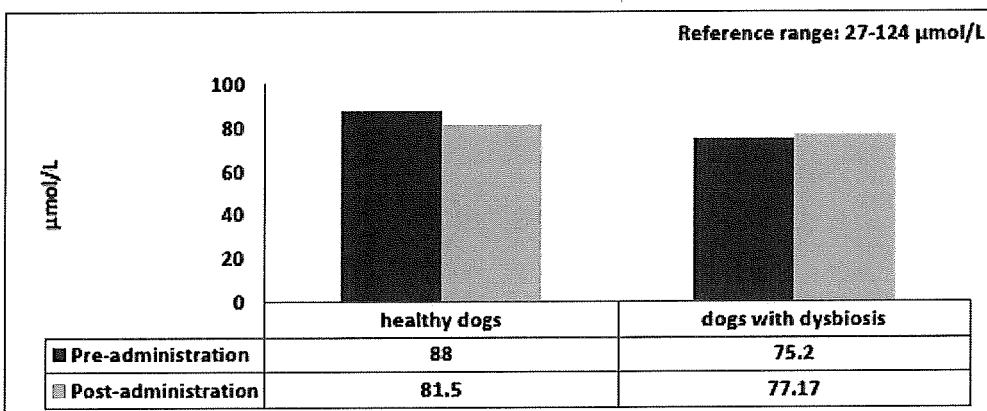
FIG. 24 is a chart showing creatinine dynamics pre-and post-administration of a probiotic composition of this invention, in healthy dogs and dogs with dysbiosis.
Figure 25:
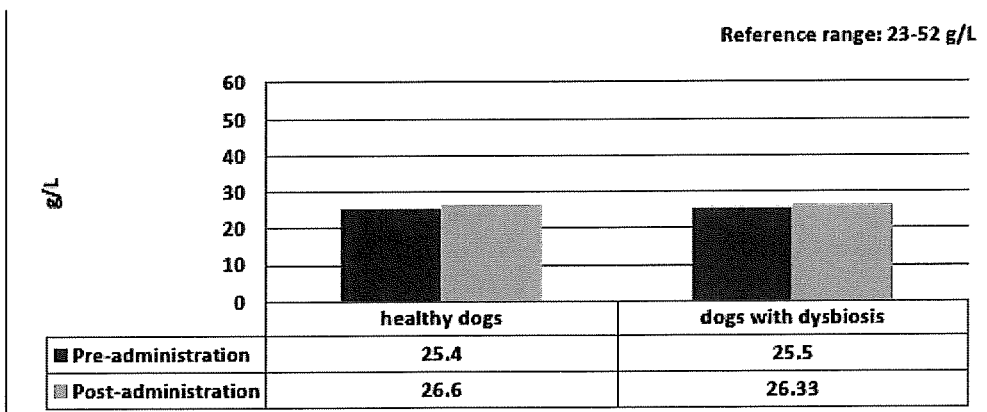
FIG. 25 is a chart showing globulin dynamics pre-and post-administration of a probiotic composition of this invention, in healthy dogs and dogs with dysbiosis.
Figure 26:
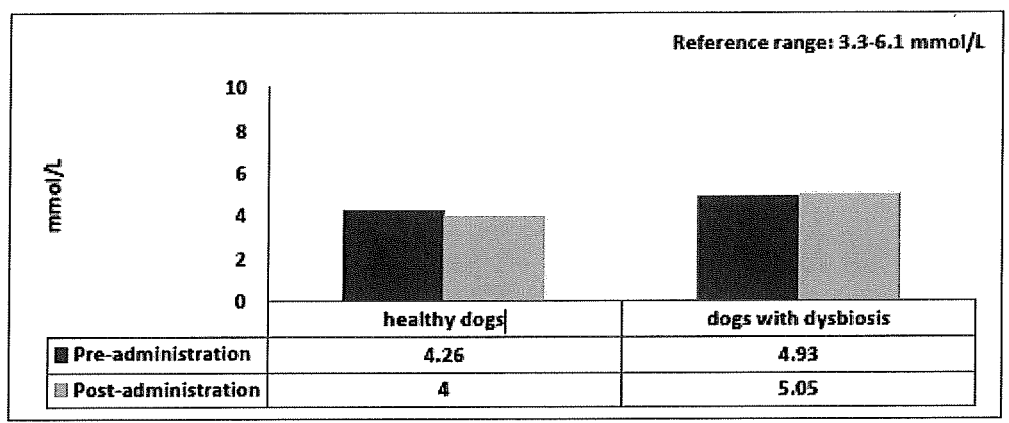
FIG. 26 is a chart showing glucose dynamics pre-and post-administration of a probiotic composition of this invention, in healthy dogs and dogs with dysbiosis.
Figure 27:
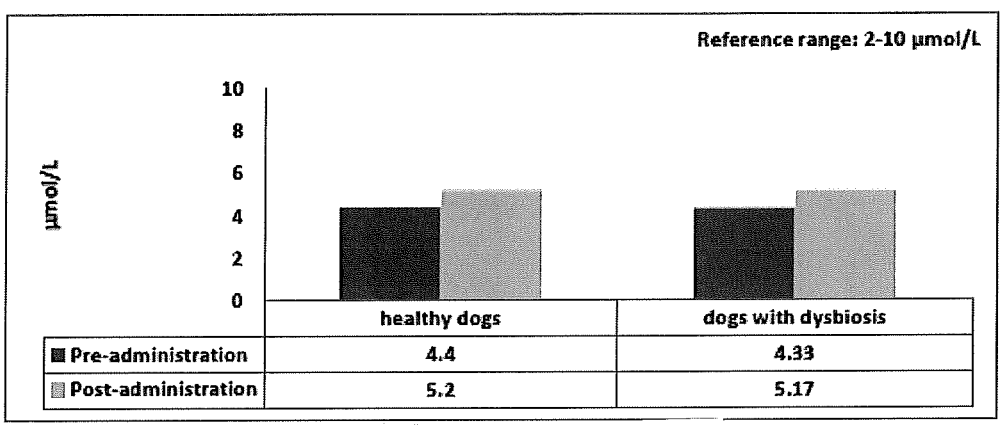
FIG. 27 is a chart showing total bilirubin dynamics pre-and post-administration of a probiotic composition of this invention, in healthy dogs and dogs with dysbiosis.
Figure 28:
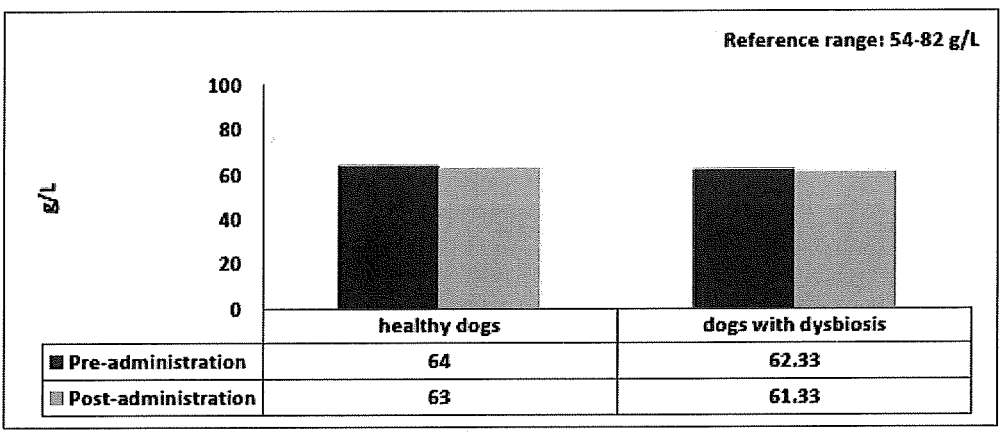
FIG. 28 is a chart showing total protein dynamics pre-and post-administration of a probiotic composition of this invention, in healthy dogs and dogs with dysbiosis.
Figure 29:
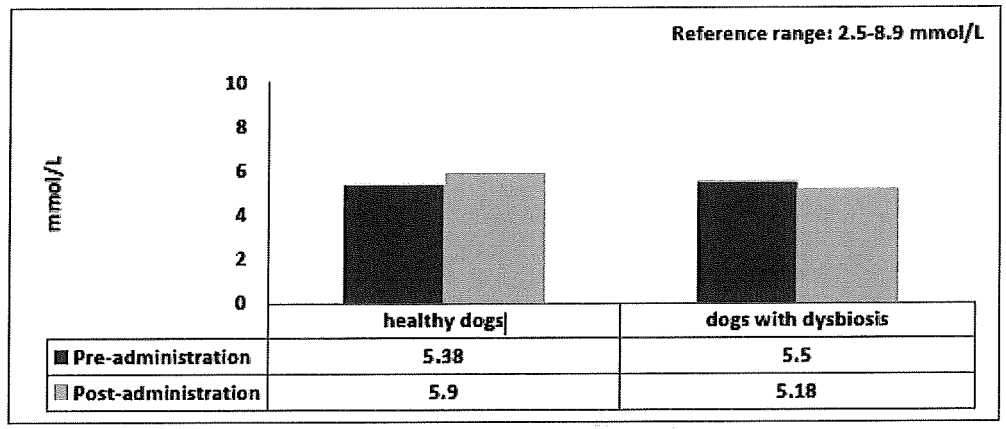
FIG. 29 is a chart showing blood urea nitrogen dynamics pre-and post-administration of a probiotic composition of this invention, in healthy dogs and dogs with dysbiosis.
Figure 30:
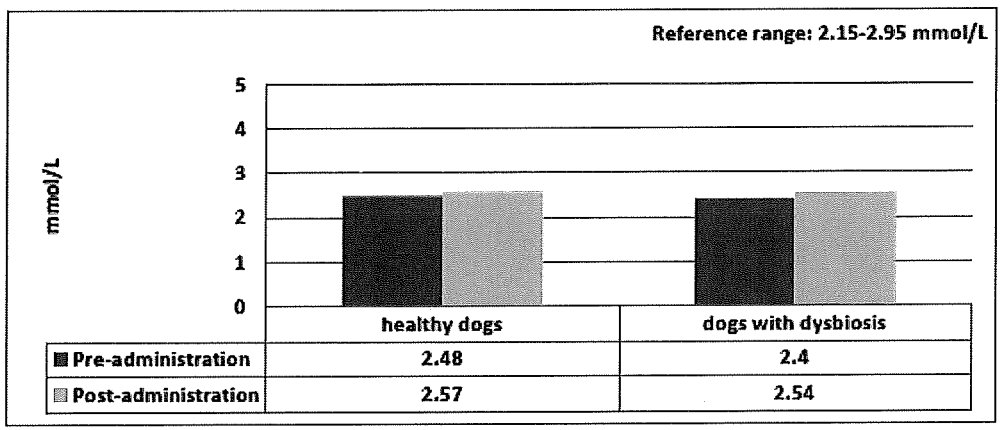
FIG. 30 is a chart showing blood calcium dynamics pre-and post-administration of a probiotic composition of this invention, in healthy dogs and dogs with dysbiosis.
Figure 31:
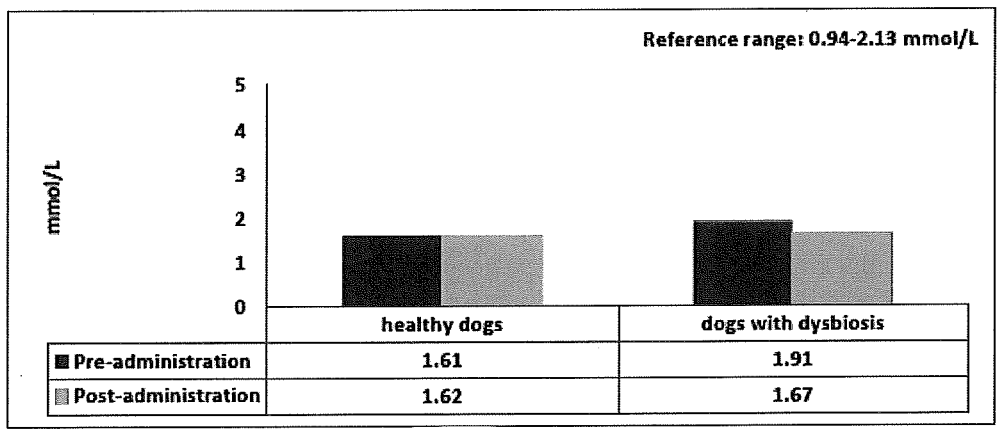
FIG. 31 is a chart showing phosphorus dynamics pre-and post-administration of a probiotic composition of this invention, in healthy dogs and dogs with dysbiosis.
Figure 32:
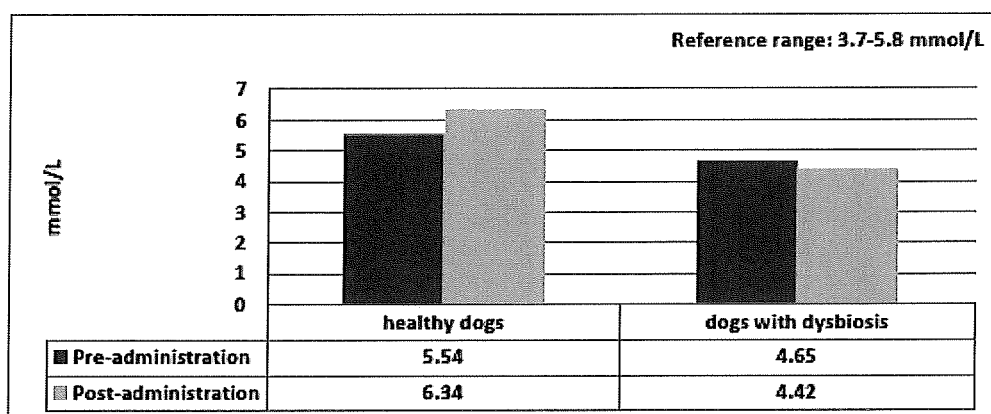
FIG. 32 is a chart showing potassium dynamics pre-and post-administration of a probiotic composition of this invention, in healthy dogs and dogs with dysbiosis.
Figure 33:
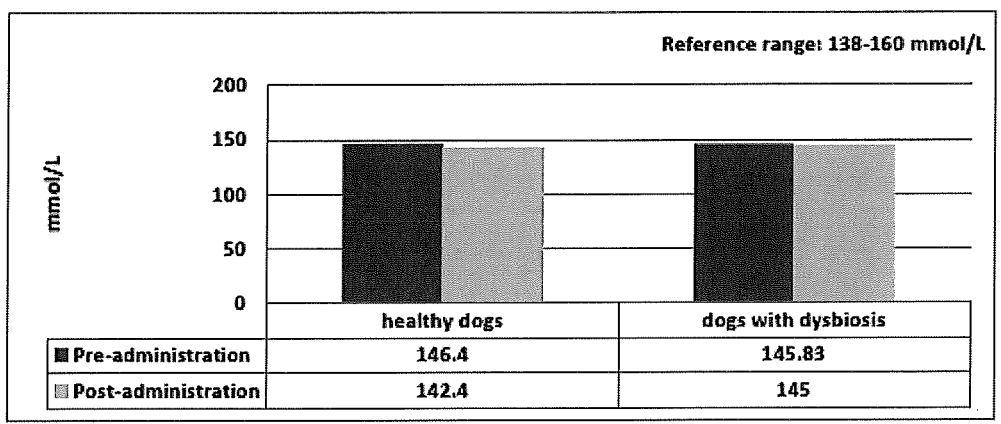
FIG. 33 is a chart showing sodium dynamics pre-and post-administration of a probiotic composition of this invention, in healthy dogs and dogs with dysbiosis.

From the point of view of the evolution of CD 14, the tendency of endotoxemia to decrease directly correlated with endotoxin levels (Table 23, FIG. 7). The correlation between the pre-and post-administration values (anti-meal) is statistically significant (p=0.05), with the correlation coefficient being r=0.08445 and $R^2$=0.744. IL1B levels remained relatively constant during the study (Table 24, FIG. 8).

FIGS. 9-33 show pre-and post-administration dynamics of hematological parameters and biochemical parameters in healthy dogs and dogs with dysbiosis.

DISCUSSION

Endotoxemia is a condition that affects the normal functioning of the gut. In veterinary medicine, metabolic endotoxemia has not been well studied. Currently available data are typically either extrapolated from human medicine or obtained from studies using dogs as a canine model for product testing. From such studies, we have learned that a small amount of endotoxin, 0.1 g/kg, was able to produce mild endotoxemia in dogs (Bartko et al., 2017). Another study attempted to establish a canine endotoxemia model by injecting a single bolus of 0.03. 0.1, or 1.0 ug/kg body weight lipopolysaccharide intravenously, which resulted in a mild endotoxemia (F. De Vries et al., 2013).

In humans, it is known that approximately 5 hours after meal consumption, an increase in endotoxin levels occurs (Kirshnan, 2017). Findings from human studies related to post-meal endotoxemia can not be extrapolated to dogs because the digestion process (i.e. enzymes used and time needed to complete food digestion) varies between individual and breeds. Moreover, the differences between the diets of dogs and humans are quite large, given that dogs are carnivores and humans are omnivores.

The type of diet a dog is fed has a major influence on the level of natural endotoxemia that they experience. In our study, patient 01-K (healthy dog group) followed a raw based diet, while the other four dogs in the healthy dog group ate only dry dog food. Because an abrupt change in diet can produce GI imbalances such as diarrhea or even vomiting, we did not change the diet of the dogs in our study. Dogs enrolled in the study followed their usual diet, with the same type of food and the same meal intervals as they were accustomed to. A close look at the endotoxemia results showed that there was a difference between patient 01-K's endotoxemia levels and that of the other dogs in the healthy dog group. Although all five of the patients in the healthy dog group met the inclusion criteria for this study, the fact that patient 01-K followed a raw based diet may have influenced the levels of endotoxin absorbed in the bloodstream after consuming a meal.

Endotoxemia can be present in dogs without any clinical signs. Moreover, it can occur in clinically healthy individuals after consuming a meal, and regardless of the fat composition of the meal. We observed that in the healthy group, the mean endotoxemia levels increased (vs. pre-meal levels) 6 hours post-meal. This observation was true both before initiating the probiotic and after completion of 30 days of probiotic treatment. Although we reported an increase in mean endotoxin levels 6 hours post-meal (vs. pre-meal) in dogs after they completed the probiotic treatment, we also observed a significant decrease in the levels of endotoxin detected before and after completion of probiotic treatment. This decrease was observed in the pre-meal and post-meal (6 hour and 12 hour) time points. When comparing endotoxin levels at day 0 and day 31, pre-meal levels decreased by 20.97%, levels at 6 hours post-meal decreased 15%, and levels at 12 hours post-meal decreased by 20.6%. These results support our hypothesis that probiotic treatment is able to improve intestinal digestion in healthy individuals, and as a result, to decrease inflammation and endotoxemia levels.

The same pattern was observed in the group of dogs that had dysbiosis. The levels of endotoxemia were higher at all three time points (pre-meal, 6 hours post-meal, 12 hours post-meal) before initiating probiotic treatment, compared with those obtained after completion of probiotic treatment. Moreover, the average percent decreases were greater compared to those in the healthy group. We reported a 25.89% decrease in pre-meal endotoxin levels (day 0 to day 31), a 35% decrease at 6 hours post-meal and a 44.93% decrease at 12 hours post-meal. This trend in decreased endotoxin levels after probiotic treatment demonstrates the efficacy and impact that probiotic treatment has on re-establishing homeostasis in the GI tract.

Currently, there are no data available regarding postprandial natural endotoxemia levels in dogs. The main hypothesis of our study was extrapolated from human medicine, where such data are available (Kirshnan, 2017). However, the digestion process of dogs and humans is not identical. The amount of time in which partially digested food stays in the stomach of dogs is between 4 hours and 8 hours, varying somewhat between individuals and breeds, while for humans the digestion process lasts about 1 hour. Another difference in the digestion process between the two species is the length of the GI tract in relation to whole body dimensions of the individual (The Canine Digestion Process, Whole Dog Journal (2019), available at https://www.wholedog-journal.com/health/digestion/the-canine-digestion-process). Such aspects may influence the time in which serum endotoxin is detectable. Considering such information, we decided to assess serum endotoxin levels at 6 hours and 12 hours post-meal consumption. In both groups of dogs, a rise in serum endotoxin levels was observed for all post-meal assessments vs. pre-meal), with small variations. This finding supports our hypothesis that after consuming a meal, serum endotoxin levels rise.

The dynamic testing of serum endotoxin levels was conducted with the purpose of identifying the optimal time to detect post-meal endotoxin levels. After analyzing our results, we have determined that there is not a particular pattern or time point that is optimal for detecting post-meal endotoxin levels. We observed an increase in post-meal endotoxin levels in all dogs studied. This observation supports the hypothesis that endotoxin levels rise after consuming a meal, which has already been demonstrated in humans (McFarlin et al., 2015; Kirshnan, 2017).

CONCLUSIONS

The data obtained from this study provide new information about natural endotoxemia levels in both healthy dogs and dogs with dysbiosis. Moreover, the spore-based probiotic administered to the dogs decreased pre-and post-treatment endotoxin levels and improved the digestion process for all canine patients enrolled in the study.

Healthy Dogs

The use of the probiotic compositions of this invention presented no adverse effects in healthy dogs. The overall functions of the dog's body were not adversely affected. Hematological and biochemical parameters showed slight changes pre-and post-administration of the present probiotic compositions, with values within the normal range. Fecal scores were improved with administration of the present probiotic compositions, and flatulence decreased. Fecal weight was widely decreased after treatment, due to increased digestibility of foodstuffs. Studies on digestibility of foodstuffs measured apparent digestibility coefficients, showing an important improvement of digestibility of all studied components (dry matter, crude fat, crude cellulose, and nitrogen free extract). Endotoxemia was analyzed ante-prandial and at 6 and 12 hours postprandial. In some dogs, post-prandial endotoxemia values increased after 6 hours, and others, after 12 hours. Overall, a decrease in endotoxin levels was observed after 30 days of administration of a probiotic composition of this invention. On average, before meals, endotoxemia decreased 20.97% between day 0 and day 31. On average, 6 hours postprandial (post-meal), endotoxemia decreased 15% between day 0 and day 31, and on average, 12 hours post-prandial, endotoxemia decreased 20.60% between day 0 and day 31. In direct correlation with the trend of decreasing levels of endotoxin was the evolution of CD14. Correlation coefficient of the two parameters ($r=0.8452$; $R^2=0.744$) indicated statistical significance ($p=0.05$). IL1B levels remained relatively constant.

Dogs with Dysbiosis

In dogs with dysbiosis, we observed a decrease and/or disappearance of digestive disorders. Improvements in the general condition of the dogs were observed, depending on the original diagnosis and pathology. Hematological and biochemical parameters showed variations depending on pathology, with beneficial changes for the subjects noted. Endotoxemia decreased before and post-administration, with average percentage differences of 25.89% (before meal, day 0 to 31); 35% 6 hours post-meal (day 0 to 31); and 44.93% 12 hours post-meal (day 0 to 31). The decreasing trend off endotoxemia, post-administration, included significant progressive dynamics ($R^2=0.9536$). The evolution of CD14 tended to decrease, correlating directly with endotoxin levels. Correlations between pre-and post-administration values ante-meal were statistically significant ($p=0.05$). IL1B levels remained relatively constant during the study.

Bioethics committee approval: This study was approved by the Bioethics Committee of the University of Agricultural Sciences and Veterinary Medicine of Cluj-Napoca.

Study procedures were conducted after fully informing each participating dog's owner of all the procedures and test products involved, and after owners voluntarily signed informed consent for their dog's participation. All study procedures were performed without harming any of the participating animals.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

The invention claimed is:

1. A method of decreasing endotoxemia in a dog comprising the steps of:
   (a) providing a probiotic composition comprising *Bacillus subtilis*, *Bacillus licheniformis*, and *Pediococcus acidilactici*, and
   (b) administering the probiotic composition to the dog in an amount effective to decrease endotoxemia in the dog.

2. The method of claim 1, wherein said *Bacillus subtilis*, *Bacillus licheniformis*, and *Pediococcus acidilactici* total about 1 billion to about 10 billion CFU.

3. The method of claim 2, wherein said CFU total is about 2.5 billion to about 5 billion CFU.

4. The method of claim 3, wherein said *Bacillus subtilis* is *Bacillus subtilis* HU58.

5. The method of claim 2, wherein said *Bacillus subtilis* is *Bacillus subtilis* HU58.

6. The method of claim 1, wherein the total amount of probiotics in said probiotic composition is about 2 billion CFUs *Bacillus subtilis*, about 500 million to 1 billion CFUs *Pediococcus acidilactici*, and about 100 million CFUs of *Bacillus licheniformis*.

7. The method of claim 6, wherein said *Bacillus subtilis* is *Bacillus subtilis* HU58.

8. The method of claim 1, wherein said probiotic composition is orally administered to the dog.

9. The method of claim 8, wherein said oral administration is for at least 30 days.

10. The method of claim 9, wherein said *Bacillus subtilis* is *Bacillus subtilis* HU58.

11. The method of claim 8, wherein said *Bacillus subtilis* is *Bacillus subtilis* HU58.

12. The method of claim 1, wherein said *Bacillus subtilis* is *Bacillus subtilis* HU58.

13. The method of claim 1, wherein said probiotic composition further comprises beef liver extract.

14. The method of claim 1, wherein said dog exhibits dysbiosis.

\* \* \* \* \*